US012783825B2

(12) United States Patent
Catchings et al.

(10) Patent No.: US 12,783,825 B2
(45) Date of Patent: Nov. 3, 2026

(54) SURGICAL PRODUCT SUPPLY SYSTEM AND METHOD

(71) Applicant: Gramercy Extremity Orthopedics LLC, Richardson, TX (US)

(72) Inventors: Jason Catchings, Richardson, TX (US); Ian Robertson, Richardson, TX (US); Paul J. Vasta, Richardson, TX (US)

(73) Assignee: GRAMERCY EXTREMITY ORTHOPEDICS LLC, Richardson, TX (US)

( * ) Notice: Subject to any disclaimer, the term of this patent is extended or adjusted under 35 U.S.C. 154(b) by 46 days.

(21) Appl. No.: 18/944,193

(22) Filed: Nov. 12, 2024

(65) Prior Publication Data

US 2025/0068866 A1 Feb. 27, 2025

Related U.S. Application Data

(63) Continuation of application No. 17/726,964, filed on Apr. 22, 2022, now Pat. No. 11,710,006, which is a (Continued)

(51) Int. Cl.

*G06K 7/10* (2006.01)
*G06K 19/077* (2006.01)

(Continued)

(52) U.S. Cl.

CPC ... *G06K 7/10356* (2013.01); *G06K 19/07758* (2013.01); *G06K 19/07773* (2013.01);

(Continued)

(58) Field of Classification Search

CPC ......... G06K 7/10356; G06K 19/07758; G06K 19/07773; G06K 7/10316; G06K 7/10346;

(Continued)

(56) References Cited

U.S. PATENT DOCUMENTS

| | | | |
|---|---|---|---|
| 6,217,978 | B1 | 4/2001 | Murase et al. |
| 8,174,392 | B1 | 5/2012 | Saghbini et al. |

(Continued)

OTHER PUBLICATIONS

Int'l Search Report and Written Opinion issued Jan. 16, 2019 in Int'l Application No. PCT/US2018/59965.

(Continued)

*Primary Examiner* — Seung H Lee

(74) *Attorney, Agent, or Firm* — Panitch Schwarze Belisario & Nadel LLP

(57) ABSTRACT

A surgical product supply system includes a cart having a first compartment and a second compartment. The first compartment has first, second, third and fourth walls. The first and second walls are constructed of radio-reflective material and the third and fourth walls are constructed of a radio-absorptive material. The first compartment has a first storage area. A first RFID antenna array is attached to the first wall and is positioned within the first storage area. The first RFID antenna array includes a first plurality of RFID antennas. A second RFID antenna array is attached to the second wall and is positioned within the first storage area. The second RFID antenna array includes a second plurality of RFID antennas. The first RFID antenna is offset relative to the second RFID antenna such that opposing central axes of the first and second RFID antennas are not colinear.

13 Claims, 11 Drawing Sheets

Related U.S. Application Data continuation of application No. 16/951,045, filed on Nov. 18, 2020, now Pat. No. 11,342,059, which is a continuation of application No. 16/620,687, filed as application No. PCT/US2018/059965 on Nov. 9, 2018, now Pat. No. 10,878,953.

(60) Provisional application No. 62/583,638, filed on Nov. 9, 2017.

(51) Int. Cl.

| | |
|---|---|
| ***G06Q 10/087*** | (2023.01) |
| ***G16H 20/40*** | (2018.01) |
| ***H02J 50/00*** | (2016.01) |

(52) U.S. Cl.
CPC ........... *G06Q 10/087* (2013.01); *G16H 20/40* (2018.01); *H02J 50/005* (2020.01)

(58) Field of Classification Search
CPC ...... G06Q 10/087; G06Q 10/08; G16H 20/40; G16H 40/20; G16H 40/40; H02J 50/005; H02J 50/20; H01Q 1/2225; H01Q 9/16; H01Q 1/1221; H01Q 7/00; H01Q 1/52
See application file for complete search history.

(56) References Cited

U.S. PATENT DOCUMENTS

| | | | |
|---|---|---|---|
| 8,340,809 | B2 | 12/2012 | Chadbourne |
| 8,770,479 | B1 | 7/2014 | Shoenfeld |
| 10,115,073 | B2 | 10/2018 | Wicks et al. |
| 10,489,619 | B2 | 11/2019 | Reno et al. |
| 10,762,411 | B1 | 9/2020 | Parshin et al. |
| 10,878,953 | B2 | 12/2020 | Catchings et al. |
| 2002/0183882 | A1 | 12/2002 | Dearing et al. |
| 2007/0046552 | A1 | 3/2007 | Marino |
| 2010/0141457 | A1 | 6/2010 | Wass et al. |
| 2014/0188496 | A1* | 7/2014 | Ramsey ............. G06Q 10/0631 705/2 |
| 2015/0332209 | A1 | 11/2015 | DeBusk et al. |
| 2016/0042313 | A1 | 2/2016 | Caputo et al. |
| 2017/0286903 | A1 | 10/2017 | Elizondo, II |

OTHER PUBLICATIONS

Int'l Preliminary Report on Patentability issued Oct. 21, 2019 in Int'l Application No. PCT/US2018/59965.

* cited by examiner

SURGICAL PRODUCT SUPPLY SYSTEM AND METHOD

CROSS-REFERENCE TO RELATED APPLICATIONS

The present application is a continuation of U.S. patent application Ser. No. 18/203,765, filed May 31, 2023, now U.S. Pat. No. 12,141,643, and titled "Surgical Product Supply System and Method," which is a continuation of U.S. patent application Ser. No. 17/726,964, filed Apr. 22, 2022, now U.S. Pat. No. 11,710,006, and titled, "Surgical Product Supply System and Method," which is a continuation of U.S. patent application Ser. No. 16/951,045, filed Nov. 18, 2020, now U.S. Pat. No. 11,342,059, and titled, "Surgical Product Supply System and Method," which is a continuation of U.S. patent application Ser. No. 16/620,687, filed Dec. 9, 2019, now U.S. Pat. No. 10,878,953, and titled, "Surgical Product Supply System and Method," which is a Section 371 of International Application No. PCT/US2018/059965, filed Nov. 9, 2018, which was published in the English language on May 16, 2019 under International Publication No. WO 2019/094683 and claims the benefit of U.S. Provisional Patent Application No. 62/583,638, filed Nov. 9, 2017 and titled "Surgical Product Supply System and Method" the entire contents of which are incorporated herein by reference in their entirety.

BACKGROUND OF THE INVENTION

Many general surgical instruments and implant devices, and more specifically those used in orthopedic surgery, have long been provided by medical device manufacturers in a steam-sterilizable or autoclavable container. The surgical instruments and implant devices are typically hand-delivered to a surgical facility by a representative of the device manufacturer in the container or tray. Prior to the surgical procedure, the hospital or surgery center autoclaves or steam sterilizes the entire tray or container and its contents to sterilize the contents in preparation for use on the patient. This process has inefficiencies of both time and money to all involved parties, and potential disruptions associated with the sterilization and delivery processes of these products to the operating room, as well as their use during the surgical procedure.

These efforts can be inefficient and costly in terms of time, money and potential risk for medical device companies and healthcare providers. Efforts to address these issues have been recently introduced in the medical marketplace in limited fashion through the use of pre-sterilized, packaged surgical implants, and to a somewhat lesser extent, associated surgical instruments. For example, kits of sterile components are being introduced such that sets of procedure-specific sterile implants and instruments are assembled for delivery to the operating room. These kits are, however, application specific, limited in scope, and cannot address unforeseen circumstances that may require additional types of implants and/or instruments beyond those provided, nor can they support cases beyond those they are specifically designed for. No known entity has attempted to provide an extended inventory range of sterile packaged implants and instruments capable of supporting a large number and wide scope of surgical procedure types. Nor has any known entity provided a means for autonomously identifying, locating, and transacting components from the selection available in a manner which not only allows rapid and efficient retrieval of the items, but also provides inventory management, surgical case management, and electronic transactions and associated documentation in support of the surgical procedure. The system and method of the preferred present invention addresses the shortcomings of the limited prior art systems that lack flexibility for procedures and cannot handle the large number and wide range of surgical procedure types encountered by typical hospitals and surgical centers. The system and method of the preferred present invention also addresses the limitations of prior art systems by permitting autonomous identification, location and movement of components from the selection available to allow rapid and efficient retrieval of items for various surgical procedures.

BRIEF SUMMARY OF THE INVENTION

Briefly stated, in a preferred embodiment, the present invention is directed to a surgical product supply system for storing, identifying and tracking surgical equipment and supplies. The supply system includes a first compartment including first, second, third and fourth walls. The first and second walls are comprised of top and bottom walls in the preferred embodiment and the third and fourth walls are comprised of side walls in the preferred embodiment. The first compartment may also include front and rear walls in the preferred embodiment. The first and second walls are constructed of a radio-reflective material and the third and fourth walls are constructed of a radio-absorptive material. The first compartment has a first storage area defined by the first, second, third and fourth walls. A first RFID antenna array is attached to the first wall and is positioned within the first storage area. The first RFID antenna array includes a first plurality of RFID antennas. A second RFID antenna array is attached to the second wall and is positioned within the first storage area. The second RFID antenna array includes a second plurality of RFID antennas. The first RFID antenna array includes a first RFID antenna defining a first antenna axis and the second RFID antenna array includes a second RFID antenna defining a second antenna axis. The first antenna axis is offset relative to the second antenna axis by an offset distance. A first plurality of surgical items is positioned in the first storage area. The first plurality of surgical items includes a first surgical item positioned within a first package and a second surgical item positioned within a second package. The first surgical item and the first package are associated with a first RFID tag and the second surgical item and the second package are associated with a second RFID tag.

In another aspect, a preferred embodiment of the present invention is directed to a mobile surgical product supply system for storing, identifying and tracking surgical equipment and supplies. The mobile supply system includes a first compartment including first, second, third and fourth walls. The first and second walls are constructed of a radio-reflective material and the third and fourth walls are constructed of a radio-absorptive material. The first compartment has a first storage area defined by the first, second, third and fourth walls. A second compartment includes fifth, sixth, seventh and eighth walls. The fifth and sixth walls are constructed of the radio-reflective material and the seventh and eighth walls are constructed of the radio-absorptive material. The second compartment has a second storage area defined by the fifth, sixth, seventh and eighth walls. A first RFID antenna array is attached to the first wall and is positioned within the first storage area. The first RFID antenna array includes a first plurality of RFID antennas. A second RFID antenna array is attached to the second wall and is positioned within the first storage area. The second RFID antenna array includes a second plurality of RFID antennas. A third RFID antenna array is attached to the fifth wall and is positioned within the second storage area. A fourth RFID antenna array is attached to the sixth wall and is positioned within the second storage area. A first plurality of surgical items is positioned in the first storage area. The first plurality of surgical items includes a first surgical item positioned within a first sterile package and a second surgical item positioned within a second sterile package. A first RFID tag is attached to the first sterile package and a second RFID tag is attached to the second sterile package. The first and second RFID antenna arrays are configured to periodically scan the first plurality of surgical items to determine a first number of surgical items in the first plurality of surgical items. A second plurality of surgical items is positioned in the second storage area. The second plurality of surgical items includes a third surgical item positioned within a third sterile package and a fourth surgical item positioned within a fourth sterile package. A third RFID tag is attached to the third sterile package and a fourth RFID tag is attached to the fourth sterile package. The third and fourth RFID antenna arrays are configured to periodically scan the second plurality of surgical items to determine a second number of surgical items in the second plurality of surgical items.

The preferred present invention relates to an inventory supply and management system and method for making implants, instruments, and other devices for general surgery and, more specifically, orthopedic surgery, available in a manner which provides an efficient and user-friendly system and method for rapidly identifying, monitoring, managing, and locating within the inventory supply system at the location, surgical products used in support of a surgical procedure.

In accordance with the preferred present invention, a mobile inventory repository and accounting system (collectively "automated CART") for providing surgical implants, instruments, and other medical devices (collectively "items") for general, and more specifically orthopedic, surgery is sufficiently large such that it may contain more than three hundred (300) individually sterile packaged items in one or more individual internal compartments, although non-sterile packaged items may also be contained either primarily or supplementary to the sterile packaged items. The automated CART is also mobile and capable of being easily relocated and sized to be accommodated within a surgical operating room, and such automated CARTs may be capable of containing up to two thousand (2000) packaged items or more. In the preferred embodiment, each packaged item within the automated CART has a radio frequency identification ("RFID") tag affixed thereto. The CART, accordingly, contains transponders capable of interacting with the RFID tags, specifically RFID antennae, controlled by an appropriate RFID reader, and designed for communication with the corresponding item RFID tags. Because the cart may contain a substantial density of RFID tagged items that contain metal, commonly used RFID transponder configurations may not provide sufficient performance in communicating with the RFID tagged items.

The application needs of the preferred embodiment of the automated CART include several conflicting requirements with respect to standard RFID technology for implementing the system, thus requiring novel configurations of the embodied components described herein. The automated CART system requires fast reads of large numbers of inexpensive tags surrounded by metallic items in a small contained radio frequency-isolated environment. Because the contents of the tagged packages are substantially metallic, the optimal choice of RFID technology is a low frequency ("LF") system, however ultra-high frequency ("UHF") systems are optimal for reading higher quantities of tags more quickly. LF systems are not as fast nor are they as effective in high tag density environments. UHF systems have difficulty reliably reading tags in a metallic environment due to substantial reflections of radio frequency ("RF") energy and detuning of tag antennas, causing a scrambled, rather than backscattered, signals. Passive inlay UHF tags are inexpensive, however, they are commonly tuned and packaged for use on dielectric (non-metallic) materials. Passive UHF tags have been, and continue to be, developed for use on or near conductive (i.e., metallic) materials, however these tags are significantly more expensive and, therefore, prohibitive for single and disposable use.

Passive UHF tags are also susceptible to mutual detuning and reduced read-range due to backscatter energy falloff at acute azimuth and elevation angles relative to the antenna plane. The automated CART typically has substantial package (i.e., tag) density and, thus, package organization and associated package label presentation is preferably effective for users to easily and reliably visually locate the desired item within the containment system. The substantial density and the associated arrangement of the packages to optimize meeting the user needs, can conflict with the optimal performance of the RFID system. Adding to the conflict, in the preferred embodiment, the automated CART system package containment size generally results in a substantial portion of the packages located within close proximity to RFID antennas, but not necessarily within the antenna beam pattern that would provide sufficient gain for adequate backscatter, thus diminishing the reliability and accuracy of tag-reads. The tag-read reliability can be improved by implementing RF-reflective surfaces within the containment space, however, backscatter from tags within high-gain regions of the beam pattern will also reflect, possibly with sufficient energy to undermine detectability of lesser-power tag emissions. Conversely, RF-absorptive material can be utilized within the containment configuration to reduce the backscatter reflective energy of tags within high antenna-gain beam regions, however, that effect negatively impacts the readability of tags in low-gain beam regions.

In a preferred embodiment, packages are arranged within the automated CART in organized rows within drawers of a mobile automated CART. Package density and label visibility within each drawer is optimized by orienting the largest surface area of a package substantially vertically. The RFID tag is placed at a location on the package surface that is sufficiently large and sufficiently distant from the enclosed metallic item, that being on the near-vertical surface. The packages are also preferably arranged such that the vertical surfaces containing the RFID tags are sufficiently distant from a neighboring tag on a package surface to avoid tag-to-tag detuning. The packages are arranged in the preferred embodiment in a plurality of drawers within the automated CART, two of which are proximate to an upper and a lower side of the containment structure, respectively. Depending on the configuration of the drawers and packages, the package tags contained in those drawers may be in very close vertical proximity of the upper or lower containment structure surfaces and may be very near the extreme boundaries of those surfaces, i.e., front, back, left or right sides, thus located outside of the optimal antenna beam region for tag reads.

To overcome the CART-imposed deficiencies of weak backscatter from tags outside high-gain regions of the antenna beam pattern, near RF-absorptive surfaces, and with non-optimal RFID tag orientations, antennas are preferably mounted on two opposing surfaces of the containment box. In the preferred embodiment, antennas are mounted on the upper and lower surfaces. Additionally, a plurality of relatively low-gain circular antennas, forming an antenna array, is typically utilized for both the top and bottom surfaces. The antenna arrays are preferably arranged such that no two opposing antennas are directly in line vertically with one another and their locations are optimized to provide sufficient gain antenna beam coverage of packages located in close proximity to the opposing antenna array as well as to the containment surface borders. Additionally, the antenna arrays in the preferred embodiment are mounted on RF reflective surfaces to augment both RF emissions from the antennae and backscatter from close-proximity tags. Low-gain antennas, e.g., approximately three decibel (3 dB) antennas, are used to counteract the otherwise significant RF energy produced by the plurality of antennas within the arrays, and thereby minimize the amount of reflected backscatter energy and optimize the readability of all tags within the containment volume in conjunction with other optimized design elements as stated herein.

In the preferred embodiment, a plurality of sub-compartments within the automated CART containment system segregate inventory items for the purposes of radio frequency isolation and item location. At least one of the sub-compartments within the automated CART retains the same features as described above regarding antennas, items, packaging, package placement, and structural materials. The RFID sensing system associated with one sub-compartment is preferably restricted to read tags only within that sub-compartment. In similar fashion, a neighboring sub-compartment RFID sensing system typically cannot read tags located in the first sub-compartment. This configuration provides for a gross means of associating specific items to a sub-compartment, thereby facilitating item searches by limiting regions of the automated CART. A finer means of item location is provided for by sequential tag-read interference of individual package tags within a sub-compartment during a RFID read session. Each item is preferably associated with a specific location within a drawer row and column by blocking, e.g., detuning, individual tag reads with the exception of one single tag, then associating the sole tag identified to that unblocked location. This process is sequentially repeated until all item locations have been read. Alternatively, session types can be used to restrict tags from reporting back once they have been inventoried, so blocking previously inventoried tags is generally not needed. The tag/location data is then stored for reference and utilized when item searches are initiated. Additionally, the automated CART preferably contains at least one RFID antenna in isolation from all compartments or sub-compartments. Items consumed, i.e., removed, from the automated CART may be identified by placing the associated RFID tag in proximity to this isolated antenna and performing a tag read, as well as by subsequent tag reads within the compartments to compare the item inventory before and after a consumption period.

In the preferred embodiment, the automated CART typically retains all item identification data obtained from the associated item RFID tag in a computational means containing physical memory. The item data stored in the RFID tag preferably includes a part number, a unique serial number, and package expiration date, however, other pertinent information useful to the surgical case or transaction of the item may also be included in the tag memory. The automated CART also has a communication means that allows wired or wireless communication to a remote server maintaining a database that can be synchronized with the data located in the automated CART computational means physical memory. As items are added or removed from the automated CART, the transactions are monitored and logged and inventory updates are sent to the remote server or central server. In similar fashion, when items are added to the remote server, e.g., new items in a main warehouse location or new part numbers, and subsequently physically added to the automated CART, the items will be scanned, added to the physical memory, and transacted through the communication means to change the inventory location on the remote server. Additionally, when items are removed from the automated CART, as determined by the method described in brief above and in detail below, transactions are communicated to the remote server and associated billing activities can be initiated automatically. Information supporting the contained items, including but not limited to item specifications, instructions for use, quantities available, surgical technique guides, and the like, maintained in the automated CART physical memory and synchronized with the remote server is made available to the user and can be provided automatically through sensing of the RFID tag associated with the item before, during, or after removal and/or consumption of the item for surgery. Also in the preferred embodiment, information linking both the item, the facility in which the automated CART is located, the surgical procedure, and/or an individual surgeon, may be stored in the automated CART computational means physical memory to facilitating locating associated surgical items within or outside the automated CART, as well as providing transactional information integral to billing, item usage patterns, procedure scheduling, inventory replenishment, and the like.

BRIEF DESCRIPTION OF THE SEVERAL VIEWS OF THE DRAWINGS

The foregoing summary, as well as the following detailed description of preferred embodiments of the surgical supply system, related instruments, related implants, related items and methods of the preferred embodiments of the present invention, will be better understood when read in conjunction with the appended drawings. For the purposes of illustrating the preferred surgical supply system and related methods, there are shown in the drawings preferred embodiments. It should be understood, however, that the preferred invention is not limited to the precise arrangements and instrumentalities shown. In the drawings.

DETAILED DESCRIPTION OF THE INVENTION

Figure 1:
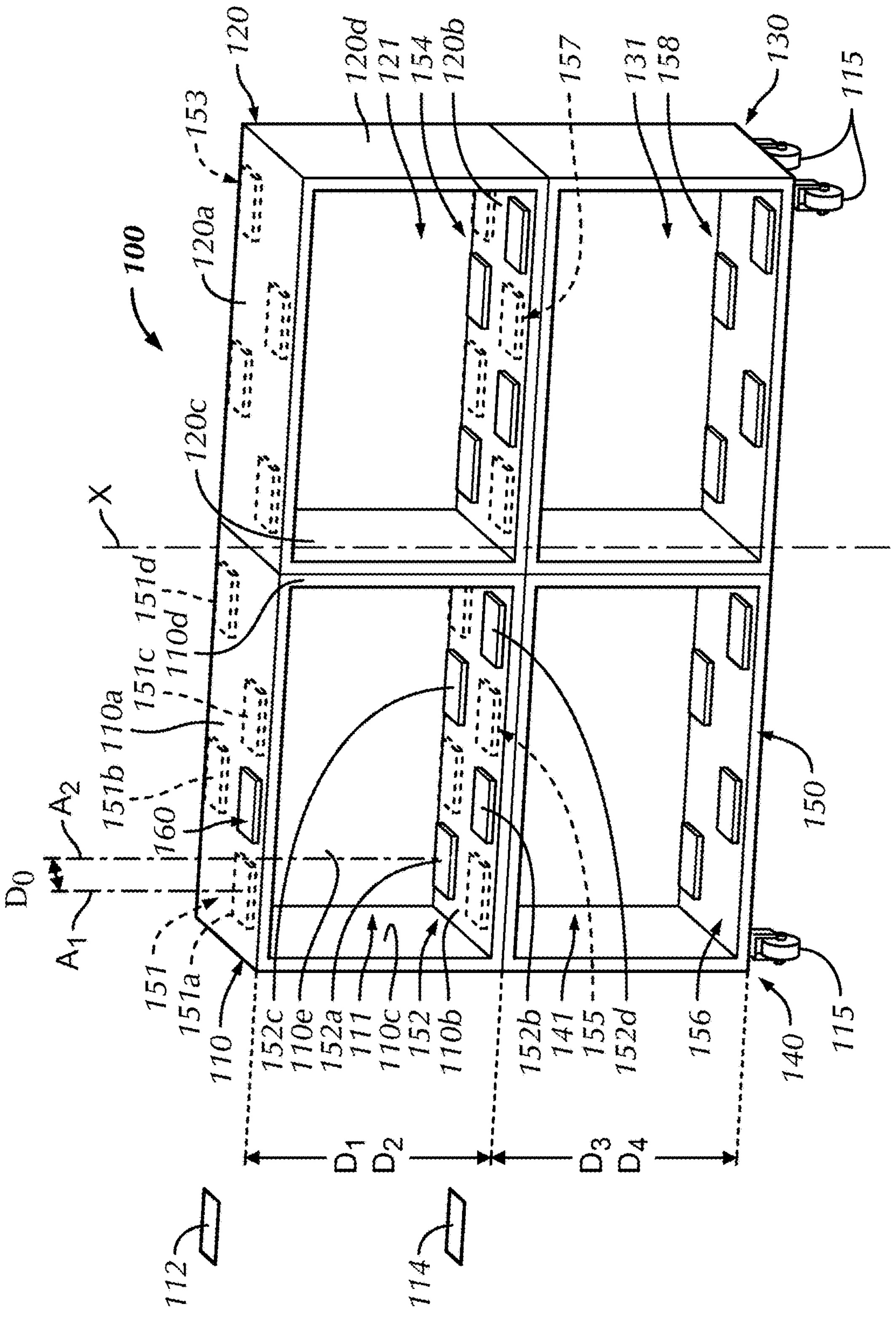
FIG. 1 is a front perspective view of a surgical product supply system including a CART in accordance with a preferred embodiment of the present invention.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred surgical product supply system and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 1-11, in the preferred embodiment of the present invention, a mobile inventory repository and accounting system (collectively "automated CART") for a surgical product supply system, generally designated 100, is utilized to provide surgical implants, instruments, and other medical devices (collectively "items") for general, and more specifically, orthopedic surgery. The automated CART and surgical product supply system 100 preferably includes containment means, sensing means, computational means, and communication means for collecting, storing, transmitting, retrieving, presenting, and processing information about the items placed therein and maintaining local and synchronized remote data regarding item retrieval and usage in a surgical procedure. Effective application of the preferred system 100 includes the automated CART to support containment of a substantially high density of items, many of which are typically constructed of metallic materials, packaged with low cost RFID tags affixed to each. Additionally, the system 100 preferably, automatically, rapidly, and accurately monitors the contained items, accounts for any transactions, and reports transactional activities to a remote server/database of the system 100.

Referring to FIG. 1, in the preferred embodiment, the surgical product supply system 100 provides a specific environment to house the inventory of items for a relatively large number of surgical procedures and supports the functions of the automated CART. This environment preferably facilitates a large number of inventory items in a space or on the CART that has a substantial density of packaged items. The system 100 preferably provides storage in a manner allowing for uncompromised functioning of the sensing means. As shown in FIG. 1, the containment means of the surgical product supply system 100 includes one or more compartments 110, 120, 130, 140, each incorporating a plurality of RFID antennas 150. The compartments preferably include a first compartment 110, a second compartment 120, a third compartment 130 and a fourth compartment 140. Each compartment 110, 120, 130, 140 is configured to contain in an organized manner a plurality of packaged surgical items, which are described in greater detail below, of substantially metallic composition (not shown), each incorporating an RFID tag to operate in cooperation with the associated RFID antennas 150. The containment means of the surgical product supply system 100 also physically houses electronic components (not shown) making up the sensing, computational, communication, and power management mechanisms for the automated CART system. The power management system includes a system for receiving power from standard alternating current ("AC") wall outlets and converting AC power to direct current ("DC") power, as well as maintaining charging of on-board power backup batteries, which allow the automated CART to be easily moved (i.e., mobile) with no or limited loss of function during or after relocation and also remain functional when not plugged in or during a limited power outage. The containment means of the surgical product supply system 100 also includes a plurality of wheels 115 allowing the automated CART to be mobile and easily relocated.

In the preferred embodiment, the first compartment 110 includes a first wall 110*a*, a second wall 110*b*, a third wall 110*c* and a fourth wall 110*d*. The first and second walls 110*a*, 110*b* are constructed of a radio-reflective material and the third and fourth walls 110*c*, 110*d* are constructed of a radio-absorptive material. In the preferred embodiment, the radio-reflective material of the first and second walls 110*a*, 110*b* is comprised of a metallic material and the radio-absorptive material of the third and fourth walls 110*c*, 110*d* is comprised of carbon-fiber sheet material. The radio-reflective material is not limited to being comprised of metallic materials and may be comprised of nearly any material that is able to take on the general size and shape of the first and second walls 110*a*, 110*b*, withstand the normal operating conditions of the first and second walls 110*a*, 110*b*, and perform the functions of the first and second walls 110*a*, 110*b*, as is described herein. The radio-absorptive material is similarly not limited to being comprised of carbon-fiber sheet material and may be comprised of nearly any material that is able to take on the general size and shape of the third and fourth walls 110*c*, 110*d*, withstand the normal operating conditions of the third and fourth walls 110*c*, 110*d*, and perform the functions of the third and fourth walls 110*c*, 110*d*, as is described herein.

The preferred first compartment 110 has a substantially boxy or cubic-like shape with the first and second walls 110*a*, 110*b* comprising the top and bottom walls, the third and fourth walls 110*c*, 110*d* comprising the side walls and a first rear wall 110*e* comprising the rear wall of the first compartment 110. The preferred first compartment 110 may also include a front wall that may be constructed of either radio-reflective or radio-absorptive material or a combination of both. The front wall and rear walls are preferably constructed of radio-absorptive material. The first compartment 110 and the additional compartments 120, 130, 140 preferably have boxy or cubic-like shapes and are sized substantially the same relative to each other, but are not so limited. The compartments 110, 120, 130, 140 may have nearly any size and shape that is able to receive and store surgical equipment and supplies therein, withstand the normal operating conditions of the compartments 110, 120, 130, 140 and perform the preferred functions of the compartments 110, 120, 130, 140. In the preferred embodiment, the first wall 110*a* and the second wall 110*b* are spaced apart at a first antenna array distance $D_1$ that is less than thirty-six inches (36"). The second compartment 120, the third compartment 130 and the fourth compartment 140 also preferably have top and bottom walls that are spaced apart at second, third and fourth antenna array distances $D_2$, $D_3$, $D_4$, respectively, that are substantially the same as the first antenna array distance $D_1$, but are not so limited, and may have different dimensions and sizes depending on designer or user preferences and limitations. The first, second, third and fourth walls 110*a*, 110*b*, 110*c*, 110*d* are not limited to being relatively planar and rectangular and may have a curved or arcuate shape, as long as the first compartment 110 defines the first storage area 111, which is able to receive and store the plurality of surgical items 210, 510 therein.

The first compartment 110, as well as the second, third and fourth compartments 120, 130, 140 of the preferred embodiment are connected to a mobile cart or include the wheels 115 such that the compartments 110, 120, 130, 140 are mobile for transport, particularly for transport around a medical facility. The compartments 110, 120, 130, 140 are not limited to being connected to a cart, having the wheels 114 or otherwise being movable, but are preferably mobile for movement of the surgical equipment and supplies about the medical facility, surgical center, hospital or generally other areas so that the surgical equipment and supplies can be utilized in different areas.

The first compartment 110 preferably has a first storage area 111 defined by the first, second, third and fourth walls 110*a*, 110*b*, 110*c*, 110*d*. The second, third and fourth compartments 120, 130, 140 also preferably have second, third and fourth storage areas 121, 131, 141 defined by their respective top, bottom and side walls. The surgical equipment and supplies are preferably positionable within the first, second, third and fourth storage areas 111, 121, 131. 141 during use.

The second compartment 120 preferably has a second storage area 121 defined by fifth, sixth, seventh and eighth walls 120*a*, 120*b*, 120*c*, 120*d*. The fifth and sixth walls 120*a*, 120*b* are preferably constructed of the radio-reflective material and the seventh and eighth walls 120*c*, 120*d* are preferably constructed of the radio-absorptive material. The fifth and sixth walls 1201*a*, 120*b* are preferably comprised of the top and bottom walls of the second compartment 120 and the seventh and eighth walls 1201*c*, 120*d* are preferably comprised of the side walls of the second compartment 120, but are not so limited and may be otherwise arranged and shaped, based on user preferences and requirements. The third and fourth compartments 130, 140 also similarly include top, bottom and side walls that define third and fourth storage areas 131, 141 for receipt of the surgical equipment and supplies. The first storage area 111 and the second storage area 121 preferably define a first volume and a second volume. The first volume is preferably less than seven cubic feet (7 $ft^3$), but is not so limited and may be smaller or larger depending on the arrangement of the first compartment 110, the surgical equipment and supplies stored in the first storage area 111 and additional factors. For example, the first volume may be approximately one to fourteen cubic feet (1-14 $ft^3$) for storing pluralities of surgical items 210 and packages 230. The second, third and fourth storage areas 121, 131, 141 preferably have the same or similar volume as the first volume and is similarly no so limited.

The preferred surgical supply system 10 includes the plurality of RFID antennas 150 attached to the first, second, third and fourth compartments 110, 120, 130, 140, preferably within the first, second, third and fourth storage areas 111, 121, 131, 141. The plurality of RFID antennas 150 are mounted to the radio reflective walls of the compartments 110, 120, 130, 140, including the first, second, fifth and sixth walls 110*a*, 110*b*, 120*a*, 120*b* and the upper and lower walls of the third and fourth compartments 130, 140. The plurality of RFID antennas 150 include a first antenna array 151 attached to the first wall 110*a* and the first antenna array 151 is positioned within the first storage area 111. The first antenna array 151 includes a first plurality of or at least two (2) RFID antennas 151*a*, 151*b*, 151*c*, 151*d* with the preferred first plurality of RFID antennas 151*a*, 151*b*, 151*c*, 151*d* comprised of four (4) RFID antennas 151*a*, 151*b*, 151*c*, 151*d* mounted to an underside of the first wall 110*a*. The plurality of RFID antennas 150 also includes a second RFID antenna array 152 attached to the second wall 110*b* and the second antenna array 152 is positioned with in the first storage area 111. The second RFID antenna array 152 includes a second plurality of or at least two (2) RFID antennas 152*a*, 152*b*, 152*c*, 152*d* with the preferred second plurality of RFID antennas 152*a*, 152*b*, 152*c*. 152*d* comprised of four (4) RFID antennas 152*a*, 152*b*, 152*c*, 152*d* mounted to a top side of the second wall 110*b*. The first and second antenna arrays 151, 152 are not limited to including the four RFID antennas 151*a*, 151*b*, 151*c*, 151*d*, 152*a*, 152*b*, 152*c*, 152*d* and may include nearly any number of RFID antennas that are able to detect the surgical equipment and supplies within the first and second compartments 110, 120, respectively. In addition, the plurality of RFID antennas 150 are not limited to utilizing RFID technology and may be otherwise comprised sensors, such as visual or other sensors that are able to detect the presence or absence of particular surgical equipment and supplies within the storage areas 111, 121, 131, 141 during operation.

The first RFID antenna array 151 includes a first RFID antenna 151*a* defining a first antenna axis A1 and the second RFID antenna array 152 includes a second RFID antenna 152*a* defining a second antenna axis A2. The first antenna axis A1 is offset relative to the second antenna axis A2 by an offset distance Do. The first and second antenna axes A1, A2 preferably extend substantially parallel relative to each other, extend generally through a center of the first and second RFID antennas 151*a*, 152*a*, respectively and extend generally parallel to a vertical axis X of the preferred surgical product supply system 10. The vertical axis X, as well as the first and second axes A1, A2 preferably extend generally vertically, but are not so limited and preferably extend substantially parallel to a sensing direction of the RFID antennas 151*a*, 151*b*, 151*c*, 151*d*, 152*a*, 152*b*, 152*c*, 152*d* of the first and second antenna arrays 151, 152. The first and second RFID antennas 151*a*, 152*a* are preferably spaced at the offset distance Do such that the first and second RFID antennas 151*a*, 152*a* detect different volumes within the first storage area 111 to detect different ones of the surgical equipment and supplies within the first storage area 111. Each of the first, second, third, fourth, fifth, sixth, seventh and eighth antenna arrays 151, 152, 153, 154, 155, 156, 157, 158 include four (4) RFID antennas, but are not so limited and preferably include at least two (2) RFID antennas, but may include more RFID antennas to cover a greater volume in the storage areas 111, 121, 131, 141. The preferred third antenna array 153 is attached to the fifth wall 120*a* and the fourth RFID antenna array 154 is attached to the sixth wall 120*b* of the second compartment 120, such that the third and fourth RFID antenna arrays 153, 154 are positioned within the second storage area 121. The fifth and sixth RFID antenna arrays 155, 156 are preferably positioned within the third storage area 131 and the seventh and eighth RFID antenna arrays 157, 158 are preferably positioned within the fourth storage area 141.

Figure 2:
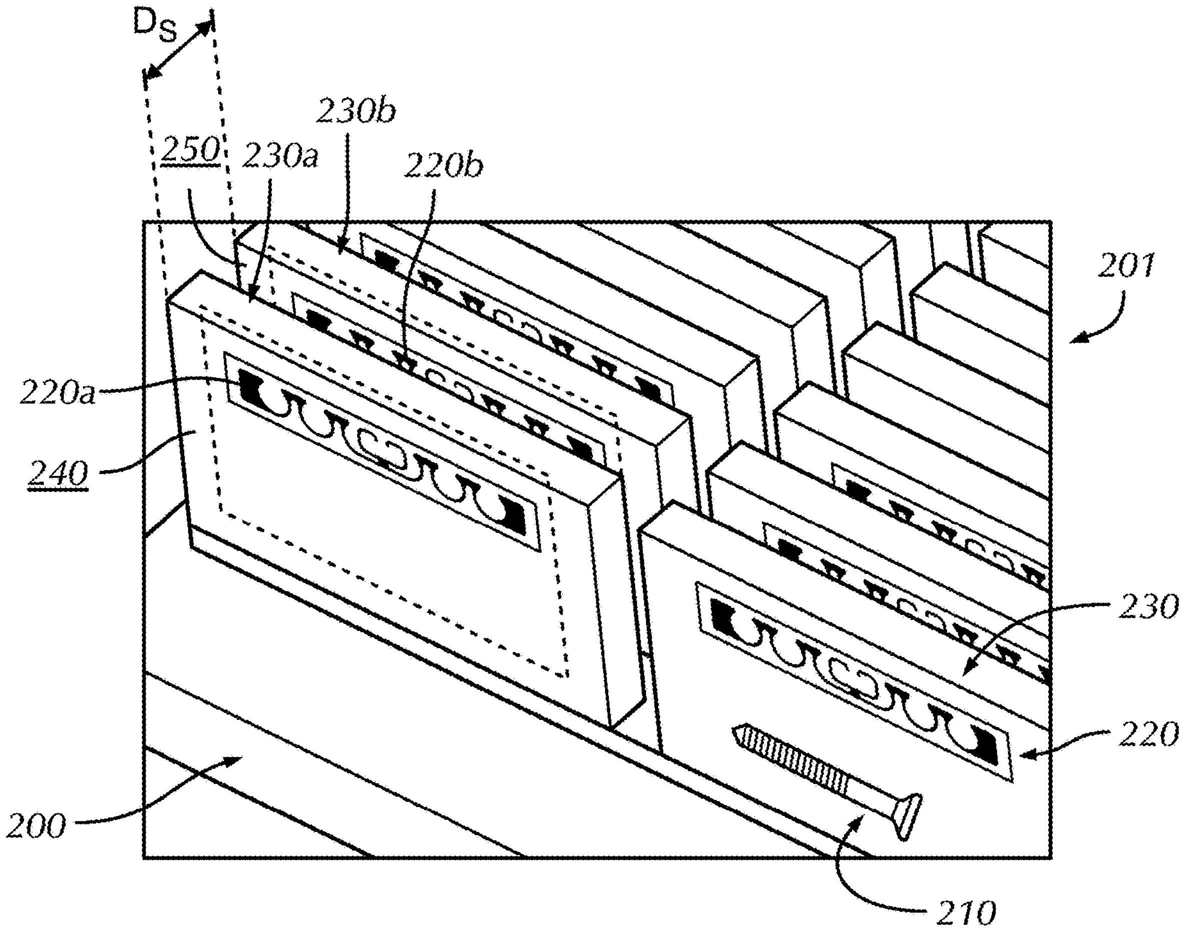
FIG. 2 is a magnified front perspective view of packaged items and associated RFID tags for placement in the surgical product supply system of FIG. 1.
Figure 9:
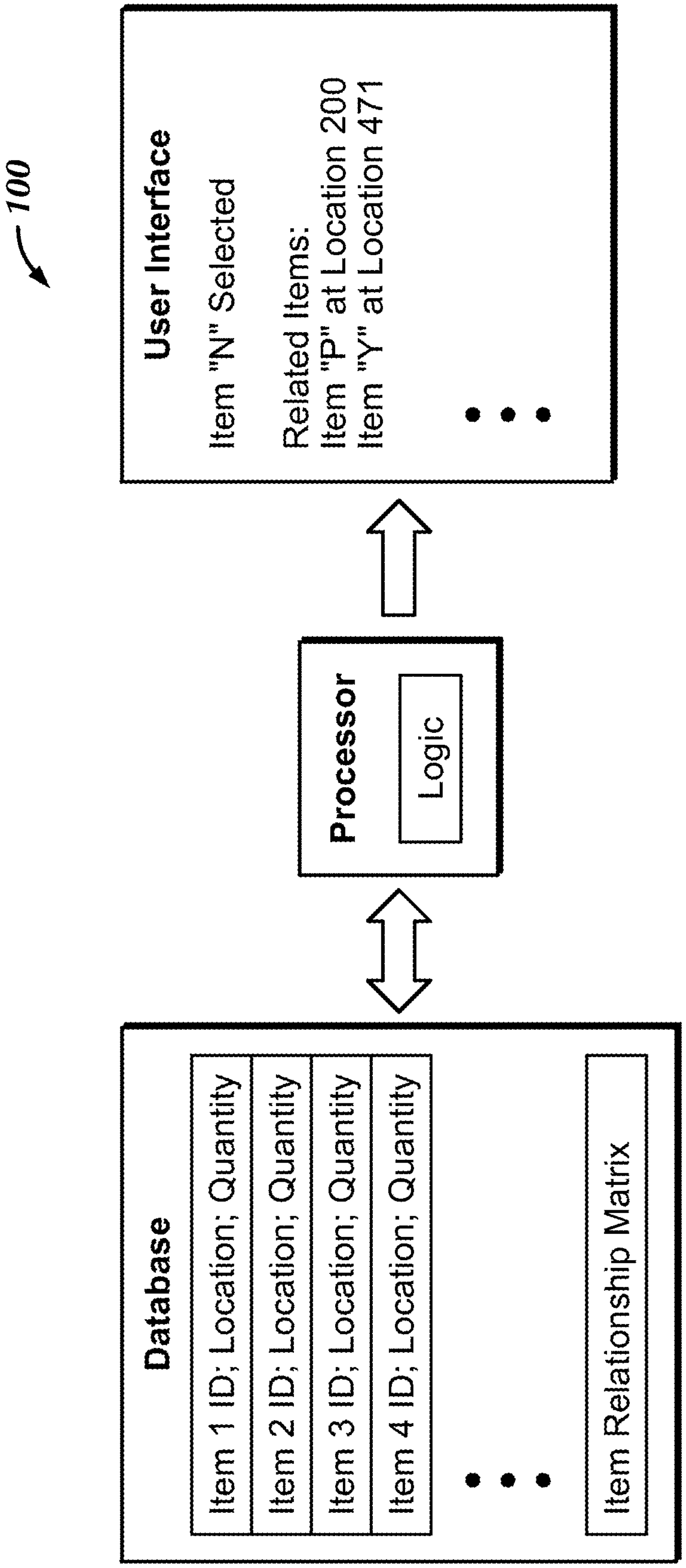
FIG. 9 is a block diagram of a local and remote databases containing item location information in accordance with the surgical product supply system of FIG. 1.

Referring to FIGS. 1, 2 and 9, for the purpose of accommodating a large number of packaged items with substantial density, a preferred example containment means 200 of the preferred embodiment allows each of the plurality of contained packaged surgical items, e.g., a bone screw 210, having one RFID tag 220 affixed to the package 230, to be arranged and held within at least one of the first, second, third and fourth compartments 110, 120, 130, 140 in an organized manner with separation distances orthogonal to first and second package planes 240, 250 of individual first and second packages 230*a*, 230*b*. The first and second package planes 240, 250 of the first and second packages 230*a*, 230*b* of the preferred embodiment are separated by a separation distance $D_S$ that is preferably no greater than two and one-half inches (2.5"), but are not so limited and may be spaced at a slightly greater distance depending on the size and shape of the item 210 or at a smaller distance. In the preferred embodiment, a substantial portion, i.e., greater than eighty percent (80%) of the contained, packaged, surgical items 210 within at least one of the compartments 110, 120, 130, 140 are organized within the respective storage areas 111, 121, 131, 141 such that the separation distances $D_S$ orthogonal to RFID tag surface planes, such as the first and second package planes 240, 250, are no greater than two and one-half inches (212") and more preferably no greater than one inch (1"). Furthermore, the separation distance $D_S$ between any of the RFID tags 220 and at least one item 210 within the associated package 230 is no greater than one inch (1"). At least one compartment 110, 120, 130, 140 is preferably capable of containing at least three hundred (300) packaged items 210. A substantial percentage of the packaged items 210 are constructed of metallic items, which are typical for surgical items 210, but are not so limited, as the items 210 may be constructed of polymeric, allograft or other biocompatible materials. The containment means of the preferred surgical product supply system 100 may include a total internal volume no greater than twenty cubic feet (20 $ft^3$) and at least one compartment 110, 120, 130, 140 may have a total internal volume of no greater than seven cubic feet (7 $ft^3$), but are not so limited and may have alternative sizes and shapes, based on user or designer requirements or preferences.

In the preferred embodiment, the containment means of the automated CART or surgical supply system 10 includes one or more substantially radio frequency-isolated compartments, such as the first, second, third and fourth compartments 110, 120, 130, 140, for the purpose of substantially isolating the RFID tag-read process within each of the compartments 110, 120, 130, 140, as well as the containment means as a whole. Each wall 110*a*, 110*b*, 110*c*, 110*d*, 110*e*, 120*a*, 120*b*, 120*c*, 120*d* of the compartments 110, 120, 130, 140 preferably contains either radio frequency reflective or absorptive material, thereby effectively containing within the storage areas 111, 121, 131, 141 radio frequency energy produced therein. In similar fashion, the compartment walls 110*a*, 110*b*, 110*c*, 110*d*, 110*e*, 120*a*, 120*b*, 120*c*, 120*d* may effectively exclude from within the storage areas 111, 121, 131, 141 nearly all radio frequency energy produced externally. Additionally, at least one of the compartments 110, 120, 130, 140 preferably has at least one containment drawer 170. The at least one containment drawer 170 preferably has an outward face 172 containing radio frequency-absorptive, a radio frequency-reflective material or a combination of radio frequency-absorptive and radio frequency-reflective material. The preferred drawer 170 is closable into the storage areas 111, 121, 131, 141 and lockable in a closed position within the storage areas 111, 121, 131, 141. The preferred compartments 110, 120, 130, 140 may include one or more drawers 170 having various sizes and shapes for containing the various packages 230 and surgical items 210 within the storage areas 111, 121, 131, 141, for example, the preferred drawers 170 shown in FIG. 11. The at least one containment drawer 170 may be comprised of a first containment drawer 170 selectively positionable within the first storage area 111 and positioned completely within the first storage area 111 in a closed position. The first containment drawer 170 may include first and second surgical items 210 that may be packaged or sterile packages or may be positioned within the drawer 170 without packaging. The preferably movable containment drawers 170 may be slidable into and out of the first storage area 111 to provide relatively easy access to the packages 230 and the surgical items 210 for the users.

In the preferred embodiment, a first plurality of surgical items 201 is positioned within the first storage area 111. The first plurality of surgical items 201 may include the bone screws 210, the RFID tags 220 and the packages 230, including the first and second packages 230*a*, 230*b* with the first and second package planes 240, 250, respectively. Reference character 201 is utilized herein to refer to a plurality of surgical items 201. A second plurality of surgical items 201, including pluralities of individual surgical items 210, such as the bone screws 210, the RFID tags 220 and the packages 230, are preferably positioned within the second storage area 121 for storage and use. The first and second pluralities of surgical items 201 are identified generically with reference character 201, but preferably include different combinations of surgical items 210 and packages 230 that each include a unique RFID tag 220 to identify the specific surgical items 210 and packages 230, as will be apparent to one having ordinary skill in the art based on a review of the present application. The surgical items 210 are similarly identified generically by reference character 210, but preferably include different surgical items 210 and may include different quantities of surgical items 210, such as multiple bone screws 210, positioned in one of the packages 230, which are similarly generically identified by reference character 230 such that any of the packages 230, whether sterile or non-sterile, may be generically identified by reference character 230. In addition, each of the packages 230 may include multiple surgical items 210 therein, such as a kit of screws 210, a bone plate 210, a surgical instrument 210 and related surgical items 210 that comprise a kit of items 210 for performing a particular medical procedure. The third and fourth compartments 130, 140 also preferably include pluralities of surgical items 210 positioned therein in a working configuration. The second plurality of surgical items includes a third surgical item, such as a bone screw, instrument, bone plate or other surgical item 210, positioned within a third package 230 and a fourth surgical item 210 is positioned within a fourth package 230. The third and fourth packages 230 are preferably sterile packages containing sterile surgical items 210 for implantation or use during the respective procedure related to the surgical item 210.

The first plurality of surgical items 201 preferably includes a first surgical item, such as the bone screw 210, positioned within the first package **230*a* and a second surgical item, such as a second bone screw 210, positioned with in the second package 230*b*. The first and second packages 230*a*, 230*b* may be sterile packages or may be non-sterile packaged, depending on the procedure, the surgical items and other factors of the manufacturer or facility where the preferred surgical product supply system 100 is utilized. The first surgical item and the first package 230*a* are associated with a first RFID tag 220*a* and the second surgical item and the second package 230*b* are associated with a second RFID tag 220*b*. In the preferred embodiment, the first RFID tag 220*a* is attached to the first package 230*a* and the second RFID tag 220*b* is attached to the second package 230*b*. The first and second RFID tags 220*a*, 220*b* are preferably attached to the first and second packages 230*a*, 230*b*, respectively, so that the removal of the packages 230*a*, 230*b* may be readily tracked by the surgical product supply system 100 and such that the surgical items and instruments 210 may be packaged without direct contact with the RFID tags 220, 220*a*, 220*b***.

The first wall **110*a* and the second wall 110*b* of the first compartment 110 preferably define a first wall plane 112 and a second wall plane 114, respectively. The first and second walls 110*a*, 110*b* and the first and second wall planes 112, 114 are positioned substantially horizontal or perpendicular to the vertical axis X in the preferred embodiment. The first and second package planes 230*a*, 230*b* are, accordingly, substantially perpendicular relative to the first and second wall planes 112, 114. This configuration results in the first and second package planes 230*a*, 230*b* being separated by the separation distance $D_S$, which is preferably less than two and one-half inches (212"), but is not so limited and may be smaller or larger depending on sizing of the packages 230 and surgical items or instruments 210** and other related factors.

In the preferred embodiment, the first and second RFID antenna arrays 151, 152 are configured to periodically scan the first plurality of surgical items 201 to determine a first number of surgical items 210 that are in the first plurality of surgical items 201. The first and second RFID antenna arrays 151, 152 preferably periodically scan the first storage area 111 to track the first number of surgical items 210 to determine if any of the items 210 are missing, have been used or additional items 210 have been added since a previous scan. The periodic scanning assists the preferred surgical product supply system 100 in maintaining inventory control of the first plurality of surgical items 210 for several reasons, such as for replenishment of items 210 that are used or for planning purposes to track the frequency of item 210 use.

The preferred surgical product system 100 also preferably includes a second plurality of surgical items 201 positioned in the second storage area 121, wherein the second plurality of surgical items 201 includes a third surgical item 210 positioned within a third sterile package 230 and a fourth surgical item 210 positioned within a fourth sterile package 230. A third RFID tag 220 is attached to the third sterile package 230 and a fourth RFID tag 220 attached to the fourth sterile package 230. Reference character 220 is utilized herein to generically identify the RFID tags 220, which are preferably attached to the packages 230 or to the surgical items 210. The third and fourth RFID antenna arrays 153, 154 are configured to periodically scan the second plurality of surgical items 210 in the second storage area 121 to determine a second number of surgical items 210 in the second plurality of surgical items 210. Similarly, the fifth and sixth antenna arrays 155, 156 periodically scan the third storage area 131 and the seventh and eighth antenna arrays 157, 158 periodically scan the fourth storage area 141 to determine the number of surgical items 210 in the third and fourth storage areas 131, 141.

The preferred surgical product system 100 is constructed with the first and second compartments 110, 120 stacked onto the third and fourth compartments 130, 140 in a generally boxy configuration with the wheels 115 to permit transport of the system 100. The first and fifth walls **110*a*, 120*a* are both preferably positioned on the first wall plane 112 and the second and sixth walls 110*b*, 120*b* are both preferably positioned on the second wall plane 114. The first and second plurality of surgical items 201 within the first and second storage areas 111, 121 are preferably positioned such that their package planes, such as the first and second package planes 230*a*, 230*b* are oriented generally perpendicular to the first and second wall planes 112, 114, respectively. In the preferred embodiment, the first, second, third, fourth, fifth, sixth, seventh and eighth antenna arrays 151, 152, 153, 154, 155, 156, 157, 158** include four RFID antennas, but are not so limited and may include less or more RFID antennas.

Figure 3:
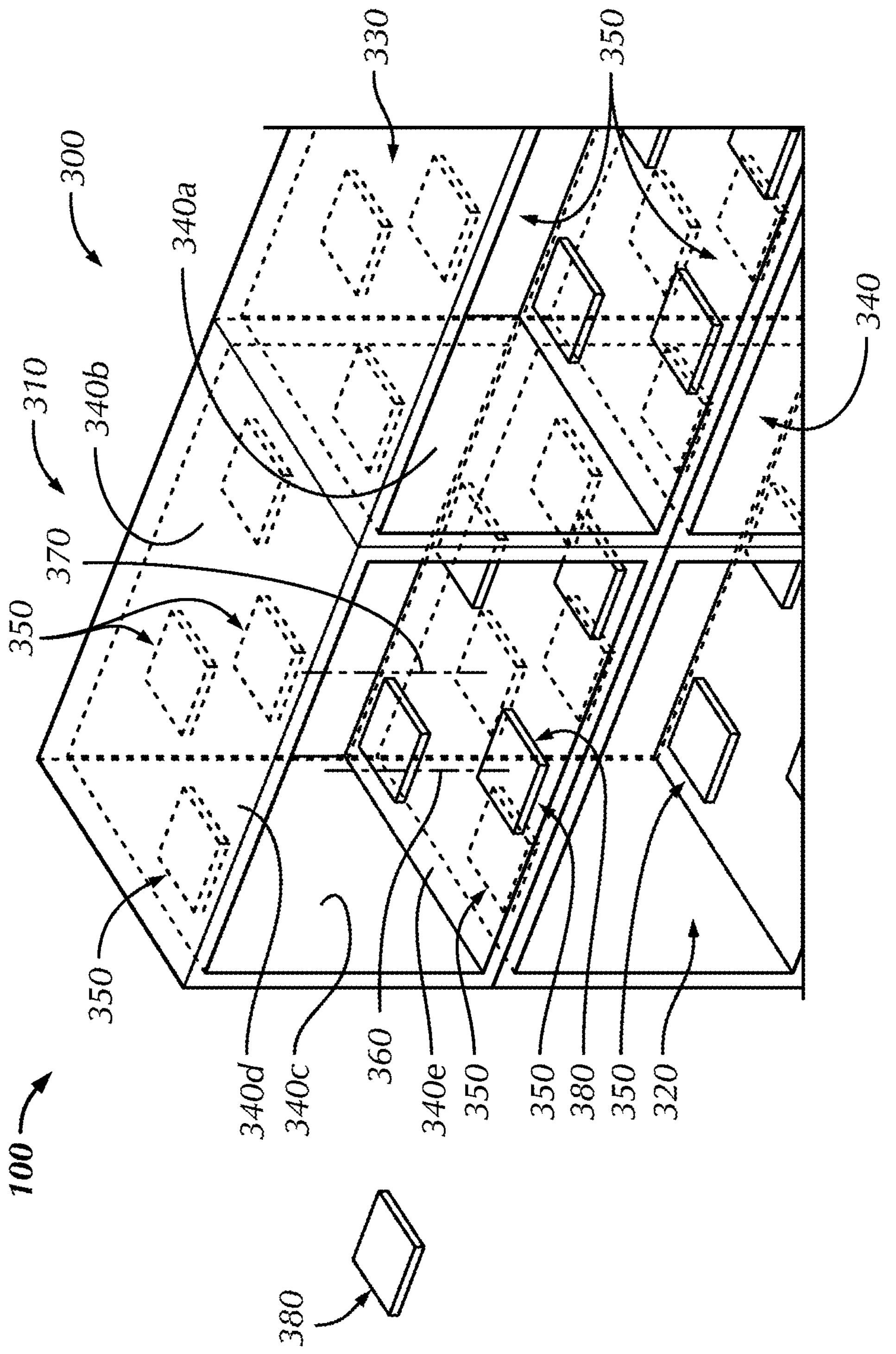
FIG. 3 is a magnified, partially transparent, front perspective view of the surgical product supply system of FIG. 1, with an RFID antenna array arrangement on the CART.

Referring to FIG. 3, alternative compartments 310, 320, 330, 340 are shown with the walls being partially transparent for clarity. Each compartment 310, 320, 330 within the containment means 300 preferably includes at least two walls **340*d*, 340*e* constructed of radio-reflective material of the six (6) walls 340*a*, 340*b*, 340*c*, 340*d*, 340*e*. The radio-reflective walls 340*d*, 340*e* are preferably constructed of a metallic material. In addition, at least two (2) of six (6) walls 340*b*, 340*c* have radio-absorptive material. The radio-absorptive walls 340*b*, 340*c* are preferably constructed of a radio-absorptive material, such as carbon-fiber. In the preferred embodiment, the top and bottom walls 340*d*, 340*e* are constructed of radio-reflective material and the sidewalls 340*b*, 340*c* are constructed of radio-absorptive material, but are not so limited. In the preferred embodiment, and top and bottom walls 340*d*, 340*e* have a plurality of RFID antennas 350 mounted to the radio-reflective walls 340*d*, 340*e* between the sidewalls 340*b*, 340*c***.

Also in the preferred embodiment, the sensing means includes a plurality of smaller ultra-high frequency ("UHF") RFID antennas 350 dedicated to detecting and identify items stored within the containment means 300. To meet the performance requirements of the automated CART, currently commercially available compact UHF antennas, with operating frequencies ranging from eight hundred sixty-five to eight hundred sixty-eight megahertz (865-868 MHz), typically in Europe, and nine hundred two to nine hundred twenty-eight megahertz (902-928 MHz), typically in the United States, with a gain of three decibels (3 dB) are preferred, however utilization of larger gain antennas is contemplated. The sensing means for the entire containment system 100 preferably performs RFID tag-reads of one hundred percent (100%) or nearly one hundred percent (100%) accuracy within a timeframe of less than ten seconds (10 sec) with at least one compartment 110, 120, 130, 140 having a minimum RFID-tagged package density of one hundred fifteen (115) RFID tags 220 per cubic foot, and no compartment 110, 120, 130, 140 having less than an eighty-five (85) tags 220 per cubic foot RFID-tagged package density. The first compartment 110 is preferably able to store approximately six hundred (600) RFID tagged surgical items 210 when the first compartment 110 has a preferred seven cubic foot (7 $ft^3$) volume. In addition, if the first compartment 110 has a volume of one cubic foot (1 $ft^3$), the first compartment preferably has the capacity of contain at least eighty-five (85) tags 220 or packages surgical items 210 and if the first compartment 110 has a volume of fourteen cubic feet (14 $ft^3$), the first compartment preferably has the capacity to container at least approximately twelve hundred (1200) tags 220 or packages of surgical items 210. In the preferred embodiment, a substantial percentage of the packages 230 within the automated CART containing metallic items. The high package density preferably results in placement of certain RFID-tagged packages 230 to be located in areas substantially close to the borders of the compartment volume. Such areas limit optimal reading of such RFID tags 220 due to antenna beam pattern restrictions, typically resulting in poor backscatter of RFID tag energy.

Still referring to FIG. 3, optimized coverage of antenna beam pattern throughout the volume of the compartments 110, 120, 130, 140, 310, 320, 330, 340 includes a plurality of RFID antennas 350 within at least one of the compartments 110, 120, 130, 140, 310, 320, 330, 340. The antennas 350 are preferably configured on opposed walls 340*d*, 340*e* in an offset array pattern such that no two opposing antennae central axes, for example, the central axes 360, 370 of opposing antennae 350 shown in FIG. 3, are collinear. The central axes 360, 340 are preferably centered on the respective antenna 350 and extend generally perpendicular to the antenna ground plane 380 of the respective antenna 350. The opposing RFID antenna arrays 350 are preferably separated at a distance no greater than thirty-six inches (36"), such as between the top and bottom walls 340*d*, 340*e*, but are not so limited. The respective opposing walls 340*a*, 340*b*, 340*c*, 340*d*, 340*e* may be alternatively spaced, such as the top and bottom walls 340*d*, 340*e* being spaced at a separation distance no greater than eighteen inches (18"), thereby separating the opposing antenna 350 at approximately eighteen inches (18").

Figure 4:
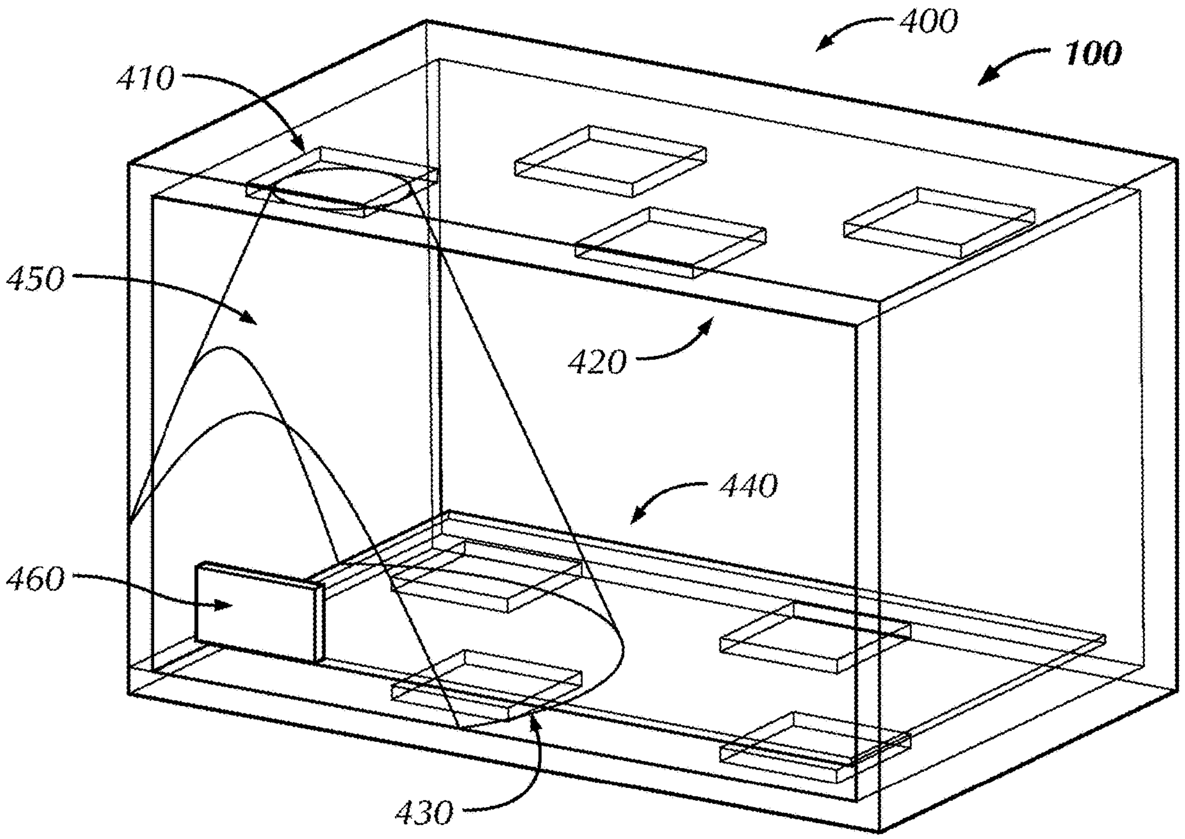
FIG. 4 is a partially transparent, front perspective view of a compartment of the surgical product supply system of FIG. 1, showing antenna placement with a beam pattern associated with the compartment.

Additionally, as shown in FIG. 4, at least one compartment 400, which is similarly constructed and arranged in comparison to the above-described compartments 110, 120, 130, 140, 310, 320, 330, 340, includes at least one antenna 410 within an antenna array 420 placed in coordination with at least one antenna 430 of an opposed antenna array 440, such that an antenna beam 450 coverage with sufficient gain includes a portion of a border of the compartment volume whereby a packaged item 460, located proximate to the compartment border, is otherwise substantially outside of the direct beam area of sufficient gain of any other antenna of the antenna arrays 420, 440.

Figure 5:
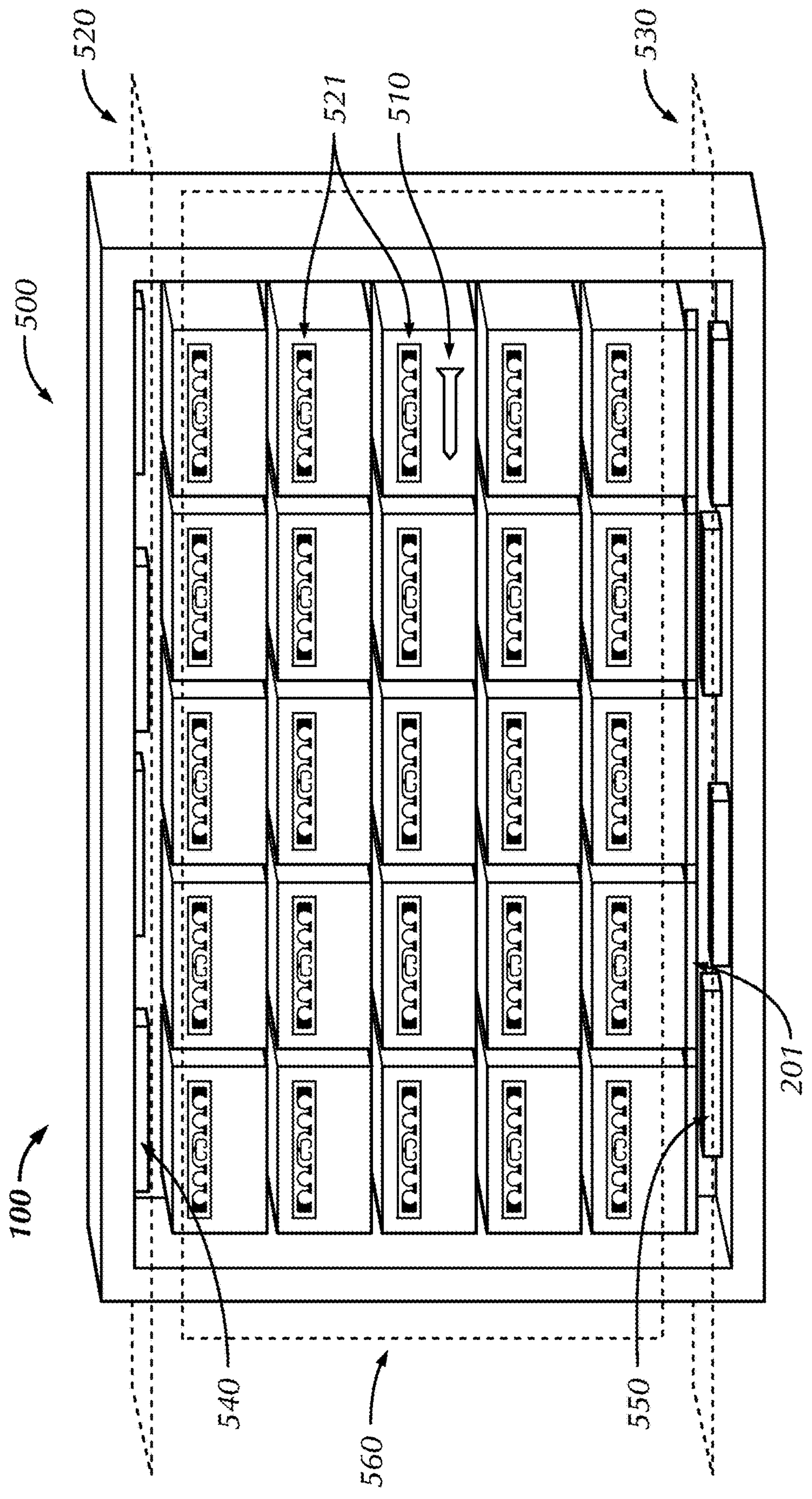
FIG. 5 is front perspective view of a compartment of the surgical product supply system of FIG. 1, wherein the compartment contains a large number of packaged items.

Referring now to FIG. 5, in at least one compartment 500, which is similarly constructed and arranged in comparison to the above-described compartments 110, 120, 130, 140, 310, 320, 330, 340, 400, at least forty percent (40%) of the locations for RFID tagged packages 510 are within four inches (4") of horizontal planes 520, 530 respectively containing opposing arrays of RFID antennas 540, 550 and at least eighty percent (80%) of the contained packaged items 510 are oriented with a surface of the RFID tag 521 substantially parallel to a substantially vertical plane 560 oriented substantially orthogonal to the horizontal planes 520, 530. In the preferred embodiment, at least one compartment of the containment means preferably has a ratio of combined antenna-mounting surface area on the one of six sides to the combined surface area (ground plane area) of the at least one RFID antenna mounted to the side no greater than four (4) and at least one compartment has a ratio of the total combined six (6) side surface area to the total combined surface area (ground plane area) of the RFID antennas no greater than twelve (12).

Referring again to FIG. 1, the containment means of the surgical product supply system 100 also has at least one extra-compartment isolated consumption antenna 160 not within any compartment 110, 120, 130, 140 and located in radio frequency-isolation to the compartments 110, 120, 130, 140. The preferred embodiment sensing means preferably has a single RFID reader for controlling all RFID antennas and on-board electronic components including RFID antennas, RFID multiplexers, an RFID reader, and a General-Purpose Input/output switch (GPIO) (not shown). It is contemplated that alternative preferred embodiments may include more than one RFID reader controlling antenna arrays either in separate compartments or shared within compartments 110, 120, 130, 140, 310, 320, 330, 340, 400.

Figure 6:
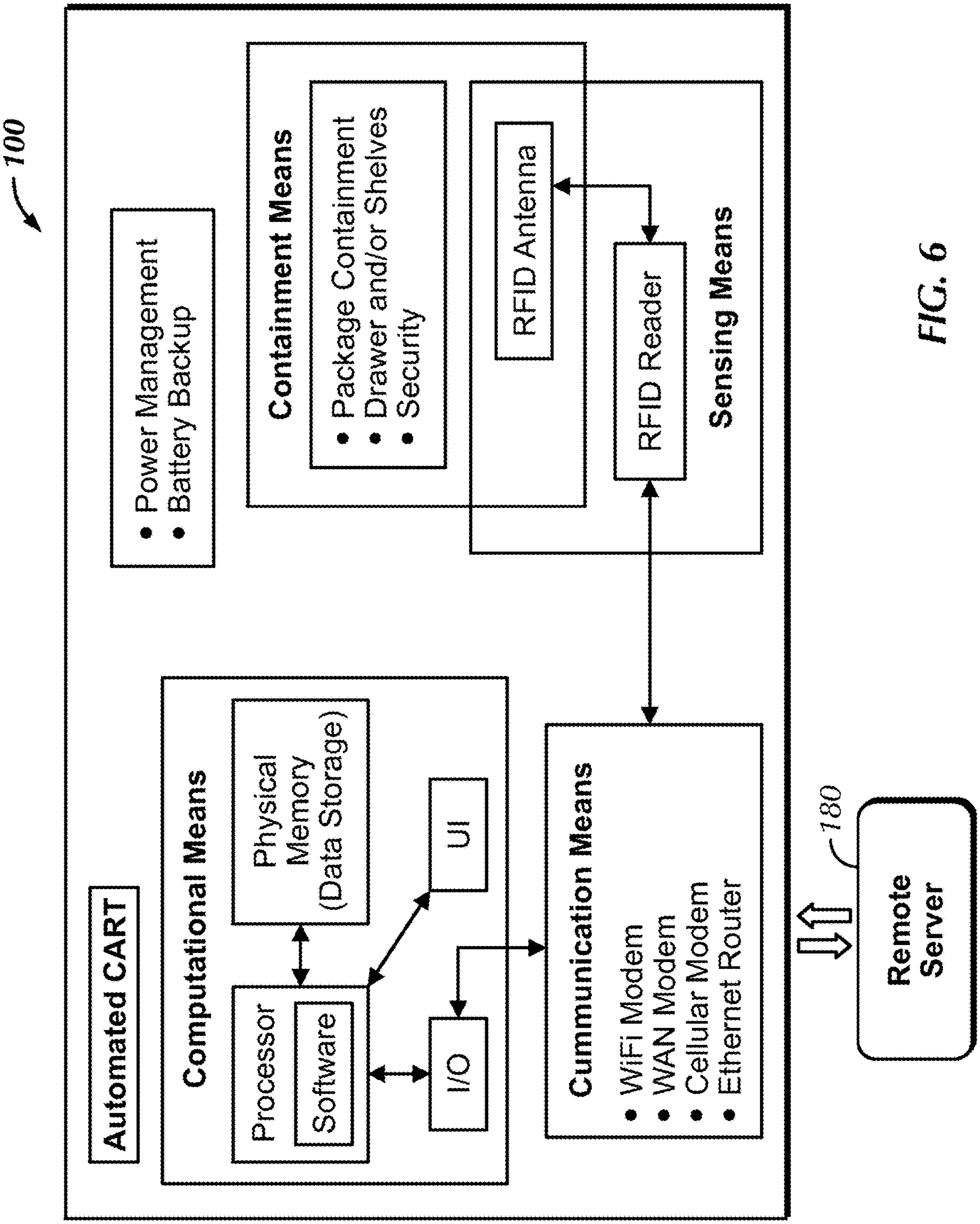
FIG. 6 is a block diagram of functional blocks making up an automated CART in accordance with the surgical product supply system of FIG. 1.

Also in the preferred embodiment and as shown in FIG. 6, the surgical product supply system 100 includes communication means. The communication means preferably comprises on-board electronic components including an Ethernet modem, a Wi-Fi modem, a cellular data modem, or a combination thereof. The communication means of the preferred surgical product supply system 100 is capable of transferring data between the sensing means and the computational means, as well as between the computational means and a remote server 180 via the internet, but is not so limited and may communicate in other mediums.

Also in the preferred embodiment and as is shown in FIG. 6, the computational means includes a computer system and associated microprocessor, data storage, input/output ports, and user interface (i.e., monitor, barcode scanner, mouse, and the like). The monitor or a combination of computer and monitor all-in-one, preferably includes a touch screen for user interaction, a speaker system for providing audio, and a microphone for receiving voice commands. The computational means incorporates software to manage and control the sensing means, allows the user interaction with the automated CART and controls communication through a modem to and from the sensing means and to and from the internet to a remote database. The software also acts through the communication means to receive and interpret data from the sensor means and manage storage of the received item data utilizing an electronic data storage means, preferably a database, to retain item data read from package RFID tags 220, as well as item information input through a user interface within the computational means, including item characteristics, surgical case data, repository inventory, item transactions, and use relationships. The software also includes the capability to identify, collect, and store RFID tag content information on one or more RFID tags 220 removed from the containment system, associate and store RFID tag content information with product information contained in a local database, synchronize a local database of product information with a remote database, synchronize a local database of surgical-related information with a remote database, and synchronize a local database of consumed product transactions with a remote database.

In the preferred embodiment, the software also includes logic algorithms to analyze electronic location information provided by the containment means to provide user-understandable location information (e.g., via a graphical user interface, LED light identifiers, and the like). The automated CART is preferably configured with a plurality of drawers, each containing a plurality of slotted inserts designed to organize and hold a sterile packaged item 210, 510 within each of the slots (See FIG. 11). The sensing means within the cart enables identification of the contents of each item 210, 510 and the specific slot location. Location identities may be determined in a variety of known ways, including providing for a single antenna for each slot and isolating each antenna/slot combination such that only the RFID tag associated with the package 230 in the corresponding slot is read. However, alternative novel means for correlating an item and its slot location is described herein. As previously described, the sensing means includes a plurality of RFID sensing antennas located strategically within at least one compartment, sufficient in number and position to effectively read all the item tags located within the compartment volume.

Figure 7:
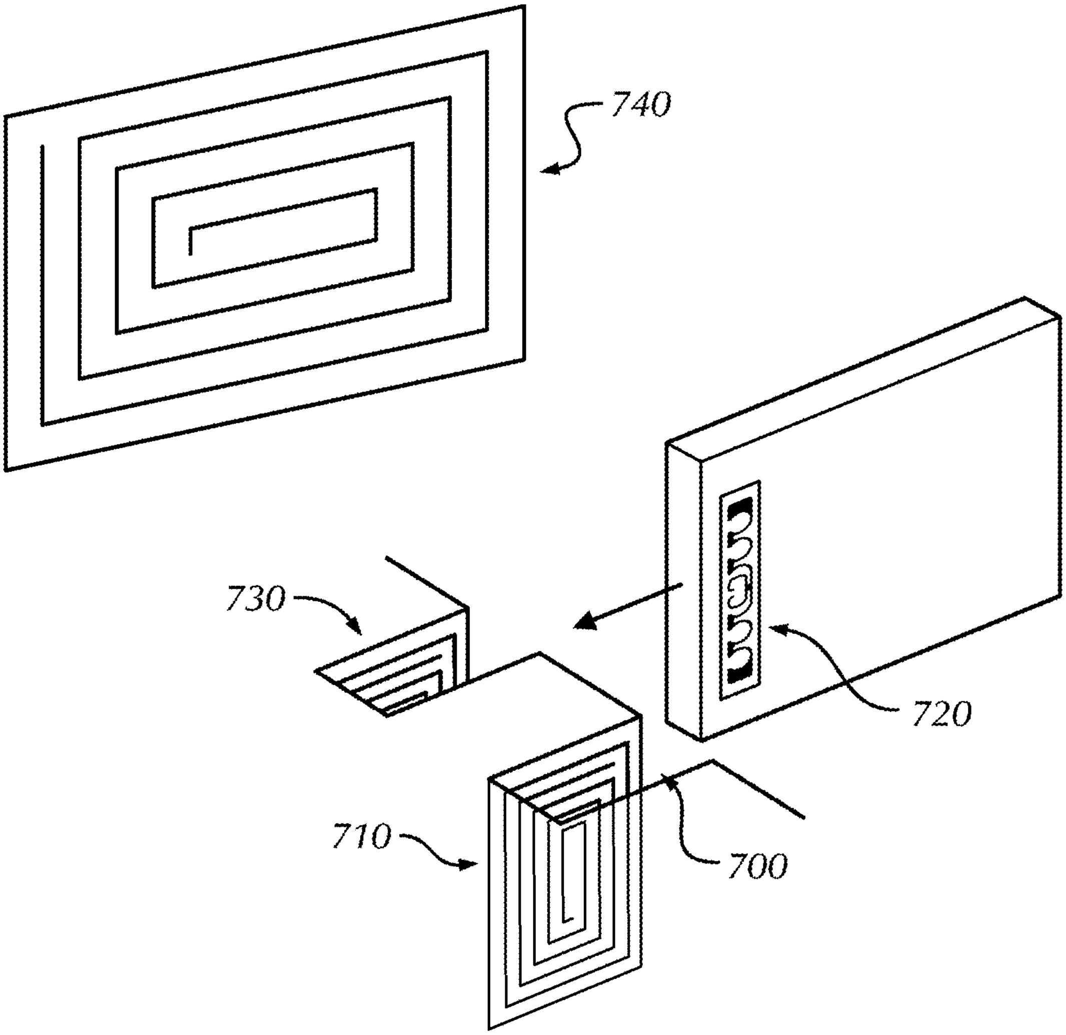
FIG. 7 is a front perspective view of a package slot of the surgical product supply system of FIG. 1, wherein the package slot includes a means to selectively read single package RFID tags to determine item location.
Figure 8:
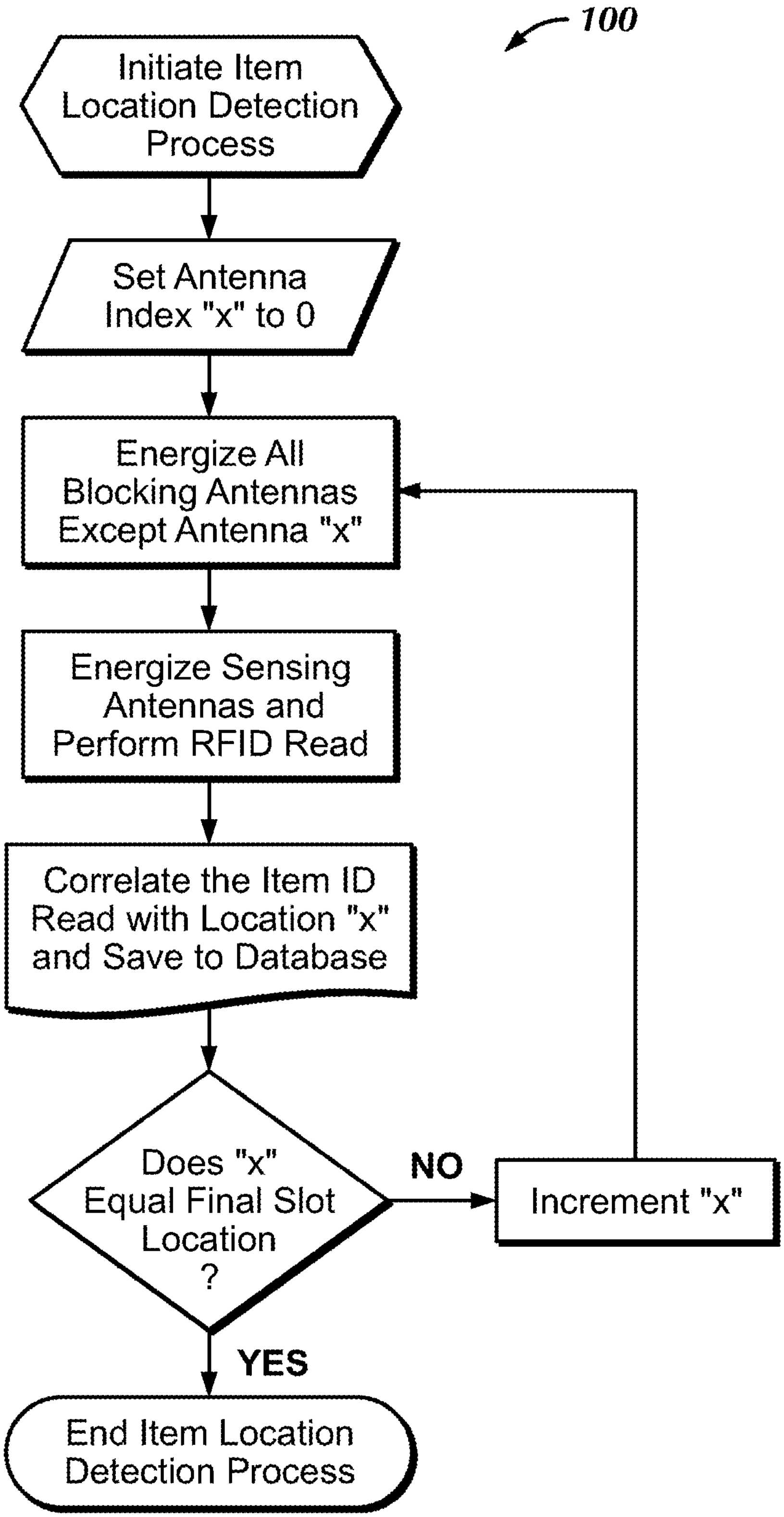
FIG. 8 is a block flow diagram of a preferred process to determine item location of a packaged item of the surgical product supply system of FIG. 1.

As shown in FIG. 7, each package slot 700 has a small blocking antenna 710 designed such that upon energization, the blocking antenna signal substantially detunes a single select item RFID tag 720 associated with that package slot 700 such that it cannot produce backscatter sufficiently and, therefore, not be detected by the sensing means antennas (not shown). Alternatively, using mechanical means rather than electronic means, a metallic blocking element (not shown) of sufficient area may be moved from a location sufficiently distant from a single select item RFID tag 220, 720 to a location sufficiently proximate to the select item RFID tag, to effectively not interfere with or effectively detune the select item RFID tag 220, 720, respectively. When in sufficient proximity to the select item RFID tag 220, 720, the metallic blocking element sufficiently detunes only the select item RFID tag 220, 710 thereby causing the select item RFID tag 220, 720 to emit scrambled and unrecognizable energy rather than backscatter energy the single select RFID tag 220, 720 would emit if not detuned. By strategically implementing the blocking antennas or metallic blocking elements at all package slot 700 locations within a specified volume, e.g., compartment, except a single slot 730, the single RFID tag 220, 720 is capable of being read during this time period is correlated to the slot 700 that does not have the blocking antenna energized, or metallic element repositioned, and subsequently this relationship between the item identity and package slot 700 location is logged to the memory of the computational means. This process is sequentially performed at all slot pairs within the specified volume thereby collecting identification data corresponding location information for all items, as shown in FIG. 8. Subsequently, this information is provided to the user via the user interface by which the user is directed to the specific slot location for retrieval of the desired item, as shown in FIG. 9.

The preferred embodiment of the containment means provides for a plurality of radio frequency isolated compartments 110, 120, 130, 140 effectively serving as gross means for an alternative embodiment to assigning locations to packaged item identification information within the automated CART. In such a configuration, packaged items are identified using the associated RFID tag information and their location is associated to the compartment 110, 120, 130, 140, 310, 320, 330, 340 from within which the tag was sensed. An additional embodiment providing for a finer location resolution utilizes a limited version of the package slot blocking embodiment that segregates location information to regions within a compartment 110, 120, 130, 140, 310, 320, 330, 340. Larger blocking antennas 740 and/or metallic blocking elements (not shown) are implemented in regions of package slots within specific drawers or areas of a compartment 110, 120, 130, 140, 310, 320, 330, 340. In a similar manner as above, all but one region would have their blocking antennas energized, or blocking metallic elements repositioned, at any one time, thereby allowing the system 100 to read the items located in the unblocked region. This then allows a limited number of items to be identified as having a location in the known region. While the system 100 would not be able to locate an item to a specific slot location as in the preferred embodiment, implementation would be less costly and it would still provide greater efficiency to the user compared to a location correlated to the whole of a compartment or automated CART.

In the preferred embodiment, the method of adding, identifying, removing, transacting, and reporting inventory items is performed by the combination of the containment means, the sensing means, the computational means, and the communication means. When a new item is added to the automated CART, the item is placed within a compartment 110, 120, 130, 140, 310, 320, 330, 340 in an organized fashion determined by the containment means and as described above for the preferred embodiment. The sensing means polls the inventory items utilizing the RFID tags 220, 720 and reports the identities of the contained items 210, 510, along with relevant item information stored in the tags 220, 720, to the computational means. The computational means recognizes the newly added items 210, 510, storing the information and also reporting the information to a remote server 180 via the communication means. Item part numbers are preferably verified against the local database within the computational means physical memory and, in the preferred embodiment, associated serial numbers for each item 210, 510 are recorded. This information is synchronized with a remote server database and item serial numbers are utilized to transact the corresponding inventory items from a previous location, e.g., a main warehouse, to the automated CART containment means location. The computational means also receives information from the remote server for any new item part number that does not have a data record in the local memory of the computational means. Such information includes specific physical and descriptive characteristics that are used to provide additional information about the item to the automated CART user for searching, reference, or instruction. This process also provides validation of part numbers and serial numbers of new items introduced into the automated CART, whereby the user is can be alerted to any item or items 210, 510 that do not have a corresponding identity, i.e., part number, serial number, or both, in the remote database, indicating a data error.

In the preferred embodiment, and in addition to serial numbers, package expiration dates are preferably included in RFID item tag data and associated within the local database to the item serial number. Alternatively, package expiration dates may be maintained in the remote database, communicated to the automated CART local database, and added to the item data record locally. Lead times ahead of the expiration date are provided by the remote database, or entered locally via the computational means user interface, for the purpose of initiating an alert indicating the impending timeline for the specific item 210, 510. The expiration alert, including the item part number, serial number, and expiration date, is communicated to the remote server and also indicated on the user interface of the communication means. The automated CART software is programmed to disallow consumption of an expired item 210, 510, when either within an expiration lead time or past the expiration date according to the instructions provided to the software. Procedures for removing expired or near-expired items 210, 510 are initiated upon acknowledgement of the computational means package expiration alert.

Figure 10:
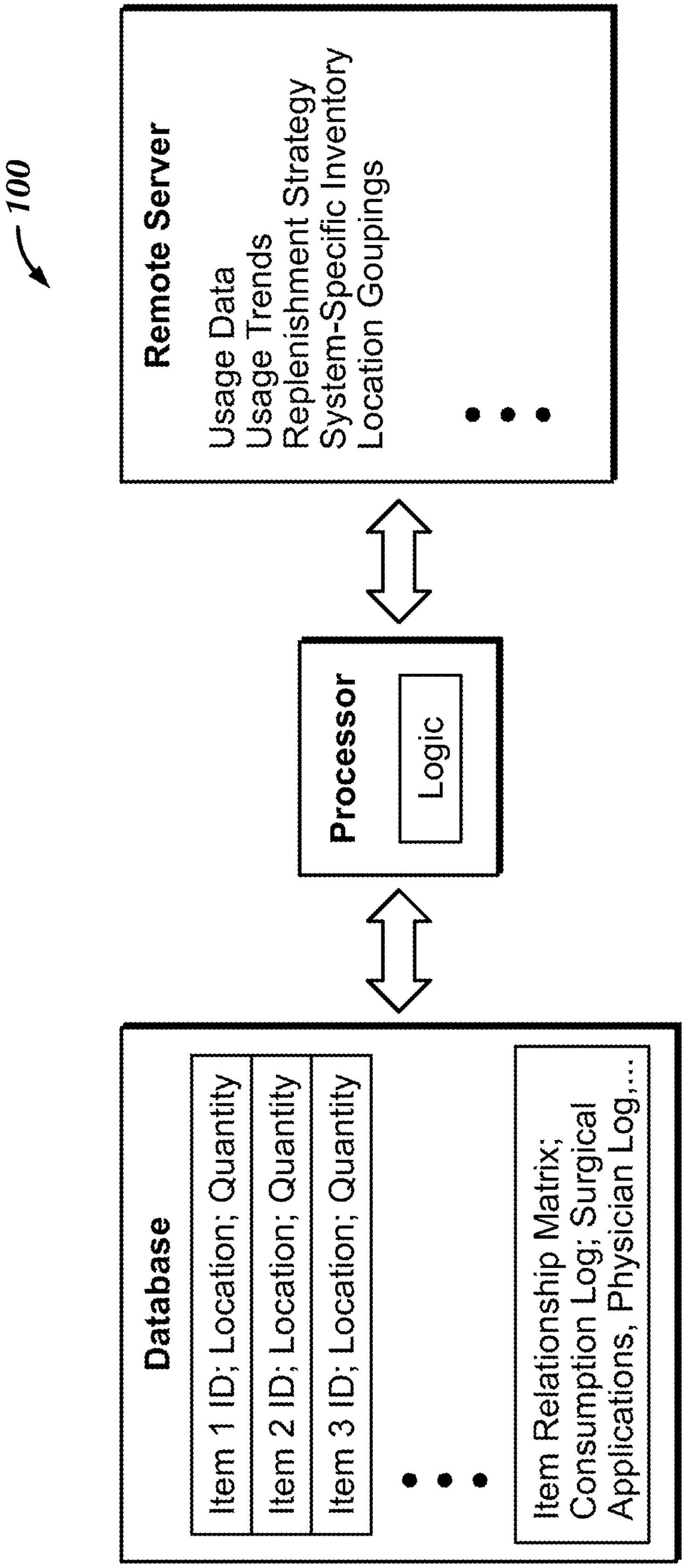
FIG. 10 is a block diagram of local and remote databases containing item/surgery relationship information in accordance with the surgical product supply system of FIG. 1.
Figure 11:
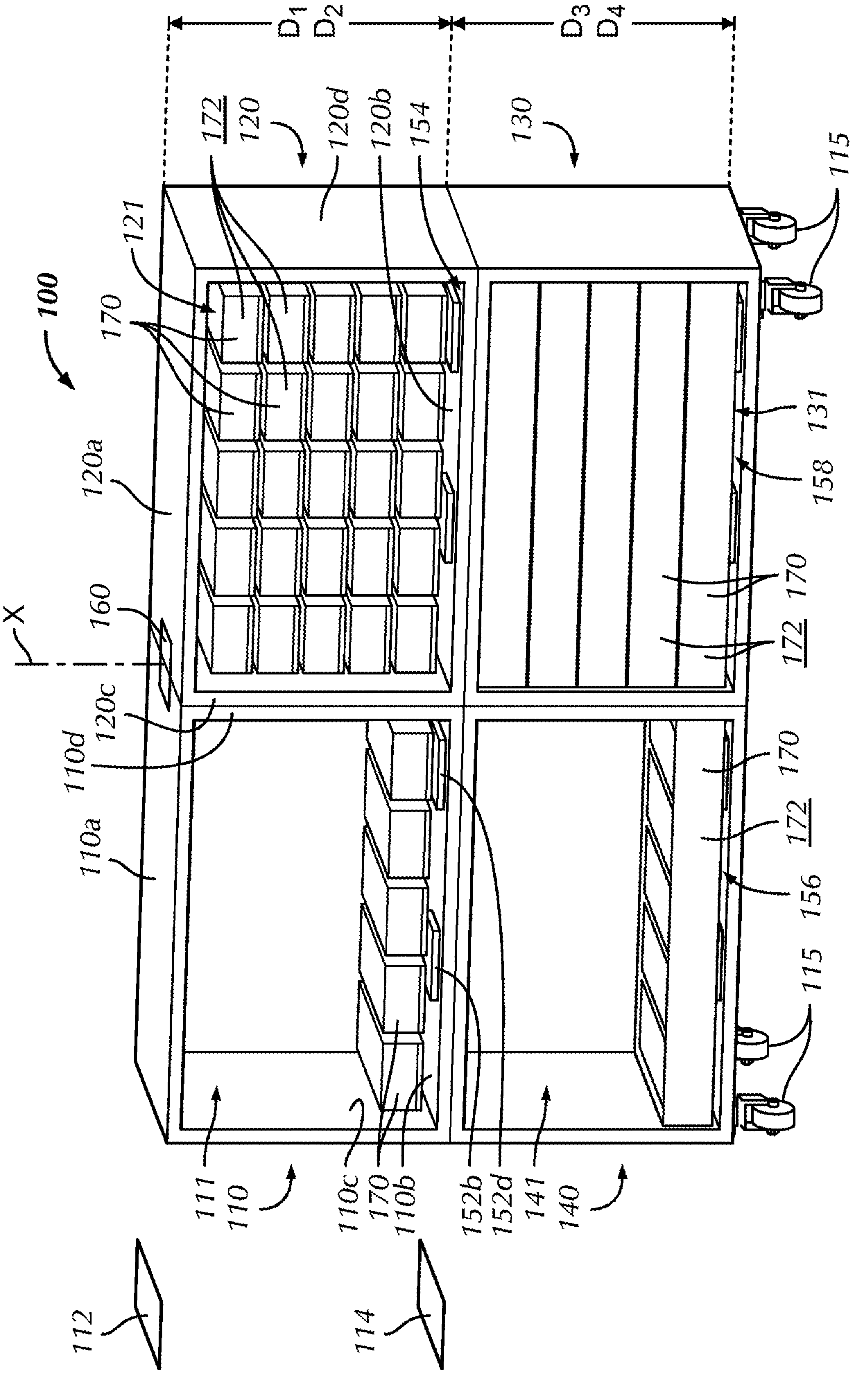
FIG. 11 is an alternative front perspective view of the surgical product supply system of FIG. 1, with different product packages and items positioned therein.

Additionally, upon removal of an inventory item 210, 510, the sensing means determines the identity or identities of the item or items 210, 510 no longer within the preferred compartments 110, 120, 130, 140. In the preferred embodiment, again referring to FIG. 1, the extra-compartment isolated consumption antenna 160 is utilized as described elsewhere herein. The removed item data, i.e., serial number that is associated with one of the RFID tags 220, is identified as having been consumed in the computational means or local server and the information is recorded locally and reported to the remote server via the communication means, such as the extra-compartment isolated consumption antenna 160. Additionally, the computational means provides a user interface that allows a consumer of the automated CART inventory items to log the items removed and consumed, i.e., used for surgery, from the containment means. The computational means then associates the item information, e.g., part number and serial number, with specific information regarding the surgical facility and other information regarding the surgical case, e.g., surgeon, body site, surgical application, etc., to create a consumption report, account for the consumption in a surgical case data record, and transfer the consumption data record to a remote server via the communication means. The specific item 210, 510, preferably identified by serial number, is then decremented from the automated CART inventory at both the local database and the remote database. Additionally, consumption transactions are electronically or manually generated and provided to the consuming entity for accounting and billing activities. These and other activities described further below are shown in FIG. 10.

An alternative consumption process is implemented within the preferred embodiment whereby the extra-compartment isolated consumption antenna 160 is not utilized by the consumer. The RFID tags 220, 720 associated with the packaged inventory contained within the automated CART are periodically scanned by the sensing means as previously described, thereby providing an updated accounting for all serial numbers held within the containment means. This item list is compared with a previously scanned contained item inventory list by the computational means, accounting for any intentionally consumed and scanned items, to determine unaccounted for items and provide an alert to both the local user and the remote database.

Consumption data for each item 210, 510 is accumulated into the local database within the computational means, whereby specific item information can be retrieved, assimilated, grouped, and filtered as required. Input from the user, through the user interface, including information regarding the relationships between the inventory items 210, 510 and surgical use, is included within the data accumulated in the local database. For example, such a relationship within an orthopedic surgical case, at a specific surgical facility, and for a specific surgeon, could define that a specific drill bit and/or screw driver 210, 510 is used with a specific screw and a specific drill guide is used with the recommended drill bit. This information would be captured periodically and accumulated over time and provided to a user through a user interface, i.e., monitor.

As an example of the utility of the system 100 in an orthopedic surgical case, operating room staff would be charged with the task of retrieving implants and instruments 210, 510 requested by the surgeon. If the above-mentioned screw 210, 510 was requested, the staff member would select the screw 210, 510 from a list presented to the user on the display. Once the item 210, 510 is selected, the software would search the database for related components and provide feedback on the proper drill bit, screw driver, and other components that are, or would likely be, used with the screw 210, 510. The staff member could then select any of the recommended components presented and be provided with the specific slot location as well as a graphical representation of the item location within the containment system. The information provided by the software thereby allows the staff member to retrieve the items 210, 510, some of which not yet requested but needed by the surgeon, in an efficient, reliable, and accurate manner.

Over a period of time, item consumption information is accumulated in the local database and transferred to the remote database through the communication means. The information is analyzed for usage trends of both specific items 210, 510 and item groups on a global basis (i.e., all deployed automated CARTS), regional basis (within a specific entity or location), and CART-specific basis. Analysis of the trends is performed to determine various usage analytics that provide the device manufacturer valuable information regarding inventory levels held within an automated CART or at the specific hospital or surgery center to increase supply chain efficiencies by influencing stocking and replenishment. Items 210, 510 more frequently used can be stocked in greater quantities while other, less used, items 210, 510 can be stocked in lesser quantities. Additionally, the consumption data across items 210, 510 is analyzed to determine use correlations, thereby influencing subsequent adjustments of on-hand quantities of related items and predictive algorithms for supply chain planning to anticipate low inventory levels and plan replenishments ahead of need and thus minimize the risk of lacking a needed item at the time of surgery.

Additionally, item location data within the containment means correlated with usage trend data provide meaningful information regarding placement of items in the containment means. Continuing with the screw example from above, items 210, 510 indicated as frequently utilized together and corresponding location information about each, are analyzed to determine placement of such items 210, 510 in close proximity, i.e., drawer and/or package slot location, within a compartment 110, 120, 130, 140, 310, 320, 330, 340 to increase efficiency in retrieving the items 210, 510. On a larger scale, information on item usage and associated trends could be assimilated across automated CARTS located at different surgical facilities to provide more generalized product organization schema where location-specific data is not available or adequate. The aggregated usage data, both for individual items 210, 510 and groups, is also analyzed to allow the manufacturer to adjust production quantities and distribution strategies, thereby reducing overall inventory levels, providing rapid item replenishment, increasing working capital, and reducing overall operating cost.

In a preferred embodiment, the communication means is connected to the internet and thus the remote server. User devices also connected to the internet are thereby available to be connected to the remote server and any or all deployed automated CARTS. Many unique capabilities provided through utilization of schemes related to the internet of things ("IoT") are contemplated through the connectivity of the automated CART. Specific to the above description, surgical staff may be connected through the internet to portals allowing access to data residing on the remote server and any one or more automated CARTS. Likewise, user information may also be provided to the one or more automated CARTS and/or the remote server. In this regard, surgical schedules, routinely maintained and communicated through the internet to the automated CART or remote server, provide information on future surgical procedures and the timing of thereof. This information is combined with surgical case information, item use data and trends, and the like to assess and predict, through the computational means of the local automated CART, the remote server, or the computational means of the user, inventory levels required to support the surgeries. This predicted inventory requirement is then compared against inventory levels in the automated CART or CARTs at the facility, nearby facilities, and/or global warehouses to determine and plan for item availability at the time and location of the future surgery.

In operation, the preferred surgical product supply system 100, which is preferably a mobile system 100, is utilized to identify, collect and store information regarding a plurality of surgical items 201 in the mobile supply system 100. The preferred surgical product supply system 100 includes a first compartment 110 having first and second RFID antenna arrays 151, 152 mounted to first and second walls 110*a*, 110*b* of the first compartment 110. The system 100 preferably receives a first plurality of surgical items 210 of the plurality of surgical items 201 into the first compartment 110 wherein each of the first plurality of surgical items 201 is associated with an RFID tag 220 of a first plurality of RFID tags 220. The first plurality of RFID tags 220 includes a first RFID tag 220 associated with a first surgical item 210 of the plurality of surgical items 201. Preferably, the RFID tags 220 are associated with one of the packages 230 that are positioned within the first compartment 110 with different varieties of surgical items 210 being positioned within the packages 230. The first and second antenna arrays 151, 152 are preferably utilized to scan the first plurality of RFID tags 220 to determine a first RFID tag content information. The first RFID tag content information is substantially comprised of a database of the first plurality of RFID tags 220, which can be utilized to correlate to the packages 230 and surgical items 210 that are in the first compartment 110 during the snapshot of time when the first compartment 110 is scanned. The first RFID tag content information is then transmitted to the local database and to the remote server 180 so that the first RFID tag content information is saved and stored. Subsequently, the first compartment 110 is again scanned with the first and second antenna arrays 151, 152 to determine a second RFID tag content information. The second RFID tag content information, similarly, provides a snapshot in time of the RFID tags 220 and, therefore, the packages 230 and surgical items 210, that are in the first compartment. The second RFID tag content information is compared to the first RFID tag content information to determine if the first RFID tag content information is different than the second RFID tag content information. If there are RFID tags 220 in the second RFID tag content information which were not in the first RFID tag content information, additional or new packages 230 and surgical items 210 were added to the first compartment 110 between the first scan and the second scan. If there are RFID tags 220 in the first RFID tag content information that were not in the second RFID tag content information, certain of the packages 230 and surgical items 210 were consumed and the system 100 is able to identify which of the packages 230 and surgical items 210 were consumed so that the consumed packages 230 and surgical items 210 can be reordered and inserted into the first compartment 110. Each of the compartments 110, 120, 130, 140 can be similarly scanned and analyzed to identify, collect and store information regarding the plurality of surgical items 201 and packages 230 that are within the compartments 110, 120, 130, 140 at any particular time and to compare the RFID tag content information at different times to track additions, consumption and replenishment of the packages 230 and surgical items 201 associated with the system 100.

In the preferred embodiment, the product information, which is preferably comprised of the packages 230 and surgical items 210 in the local database or the remote server 180 with the first RFID tag content information to identify a first set of surgical products 210 that are associated with the first plurality of surgical items. Accordingly, the system 100 is able to determine at any particular time which and how many packages 230 and surgical items 210 are within the compartments 110, 120, 130, 140 for use at the medical facility. The local database and the remote server 180 can communicate with various entities, such as billing, sourcing, planning, third party suppliers and related entities to track and maintain inventories of surgical items 210 for an organization, such as a hospital or surgical center.

The system 100 is also preferably able to determine a first consumed product set based on the comparison of the second RFID tag content information and the first RFID tag content information, specifically when the comparison of the second RFID tag content information reveals that there are less RFID tags 220 identified in the second RFID tag content information in comparison to the first RFID tag content information. This preferably results in the system 100 identifying the missing RFID tags 220, which can be correlated to particular packages 230 and surgical items 210, as consumed or used between the first scan and the second scan. The system 100 is also able to notify the remote server 180 of the first consumed product set and direct an inventory system to deliver a first replacement product set associated with the first consumed product set to the first compartment 110. The first consumed product set is preferably comprised of the consumed packages 230 and surgical items 210 between the first scan and the second scan or may include packages 230 and surgical items 210 that are identified by the extra-compartment isolated consumption antenna 160 as being consumed.

The system 100 may further scan the first compartment 110 with the first and second RFID antenna arrays 151, 152 to confirm the first plurality of surgical items 201 are present in the first compartment. If there is no difference between the first RFID tag content information and the second RFID tag content information, such that all of the identified RFID tags 220 are the same at the two different time periods, the system 100 determines that no packages 230 or surgical items 210 have been consumed and, similarly, no packages 230 or surgical items 210 have been added to the compartment 110, 120, 130, 140. The system 100 may also determine, following at least two scans that newly added surgical items 210 are in the compartment 110, 120, 130 140 if the first RFID tag content information is different than the second RFID tag content information by determining that more RFID tags 220 are in the second RFID tag content information that are identified in the first RFID tag content information. The system 100 preferably stores newly added item information related to the newly added surgical items 210 in the local database and transmits the newly added item information to the remote server 180. The remote server 180 preferably identifies the newly added surgical items 210 and transmits the identified newly added surgical items 210 to the local database or may transmit an indication that the surgical items 210 are unknown.

The system 100 may also receive, from the remote server 180, expiration dates for a first plurality of expiring surgical items 210 associated with the first plurality of surgical items 201 in response to communicating with the remote server 180, including item part numbers and item serial numbers related to the first plurality of expiring surgical items 210. Such expiration dates are preferably tracked for surgical items 210 that have a predefined shelf life and may also be utilized to identify surgical items 210 that are recalled or instruments 210 that require refurbishment or repair following predetermined usage.

The system 100 may also determine a first consumed product set based on the comparison of the second RFID tag content information and the first RFID tag content information and create a consumption report based on the first consumed product set. The consumption report can be utilized by surgical or medical provider personnel to control inventory, plan for replenishment programs, accounting and related tasks.

The preferred system 100 may also receive information related to a surgical procedure at the local database, preferably prior to conducting the surgical procedure, identify a set of procedure specific surgical items 210 that are required to perform the surgical procedure and display location information for the set of procedure specific surgical items 210 to the user or medical professional. The display of location information may include identifying locations within the first compartment 110 where the set of procedure specific surgical items 210 are stored in the first compartment so that the user is able to quickly and easily obtain the procedure specific surgical items 210 during the procedure or is readily able to plan for the procedure, including securing surgical items 210 that the professional is aware are not in the compartments 110, 120, 130, 140.

The preferred system 100 is able to monitor, at the remote server 180, the sensing, transmitting, scanning, comparing and determining steps to produce usage data, usage trends, replenishment strategies, system-specific inventory and location groupings related to the plurality of surgical items 210.

The preferred system 100 receives, at the local database, surgical schedules for a facility associated with the mobile supply system, predicts inventory levels of surgical items 210 in the compartments 110, 120, 130, 140 required to support the surgical schedules, compares the required inventory levels to the first plurality of surgical items 210 and determines required surgical items 210 to support the surgical schedules. This permits virtual planning for various surgical procedures that will be performed in the facility and may also factor procedures that are not specifically planned, but may occur based on historical procedure information.

The system, preferably at the local database or the remote server 180, may also determine if any of the RFID tags 220 identified in the second RFID tag content information is different than a stored RFID tag catalog. The stored RFID tag catalog is preferably stored in the local database or the remote server 180 and includes a listing of all known RFID tags 220 and associated packages 230 and surgical items 210. The system 100 may request identifying information for any unknown RFID tag 220 that is not listed in the stored RFID tag catalog.

The system 100 may in addition, receive, at the remote server 180, a consumed RFID tag information from the extra-compartment isolated consumption antenna 160, to indicate that one of the first plurality of RFID tags 220 was consumed. If surgical case information, i.e., surgeon, case number, user identification information, etc., is entered into the local database, this surgical case information is also communicated to the remote server 180 in association with the first plurality of RFID tags 220 consumed. The user preferably scans the RFID tag 220 at the extra-compartment isolated consumption antenna 160 after using the surgical items 210 in the associated package 230 to confirm with the system 100 that the particular package 230 and associated surgical items 210 were consumed and are no longer in the compartment 110, 120, 130, 140.

The system 100 is also able to receive, at the remote server 180 or the local database, a consumed RFID tag identifier from the extra-compartment isolated consumption antenna 160 identifying a consumed surgical item 210 and compare the consumed RFID tag identifier to the second RFID tag content information to determine if the consumed surgical item 210 is identified in the second RFID tag content information. The remote server 180 or the local database preferably removes the consumed surgical item 210 from the second RFID tag content information if the consumed surgical item 210 is identified in the second RFID tag content information. In addition, the remote server 180 or the local database preferably sends a signal indicating that the consumed surgical item 210 was consumed if the comparison of the consumed RFID tag identifier to the second RFID tag content reveals the consumed RFID tag identifier is not included in the second RFID tag contents.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the present disclosure.

We claim:

1. A method of controlling inventory levels of a surgical product supply system including, a remote server, a first CART having a first storage area, a second CART having a second storage area, a plurality of surgical items associated with a plurality of tags, respectively, that are stored in the first and second storage areas, a first sensor associated with the first cart and a second sensor associated with the second CART, the method comprising:

receiving a first CART inventory level from the first CART at the remote server based on a scan made by the first sensor, the first CART inventory level including a first plurality of surgical items of the plurality of surgical items positioned in the first storage area;

receiving a second CART inventory level from the second CART at the remote server based on a scan made by the second sensor, the second CART inventory level including a second plurality of surgical items of the plurality of surgical items positioned in the second storage area;

receiving surgical schedules associated with the first and second CARTs; and predicting a required inventory level for the first and second CARTs to support the surgical schedules based on the surgical schedules.

2. The method of claim 1, wherein the remote server predicts the required inventory level for the first and second CARTs, the remote server utilizing historical procedure information and the surgical schedules to predict the required inventory level for the first and second CARTs.

3. The method of claim 1, wherein the surgical schedules are received at a local database, the local database predicting the required inventory level for the first and second CARTs.

4. The method of claim 1, further comprising:
comparing the required inventory level to the first and second CART inventory levels; and
determining required surgical items to support the surgical schedules.

5. The method of claim 1, further comprising:
conducting virtual planning for surgical procedures associated with the surgical schedules.

6. The method of claim 1, wherein the surgical schedules are for a surgical facility and the surgical schedules include timing associated with surgical procedures associated with the surgical schedules.

7. The method of claim 1, wherein surgical case information, item use data and trends and the surgical schedules are used to predict the required inventory level for the first and second CARTs.

8. The method of claim 1, further comprising:
comparing the required inventory level for the first and second CARTs against the first and second CART inventory levels, inventory levels of nearby facilities and inventory levels of global warehouses; and
determining a plan for surgical item availability at a time and location of a future surgery of the surgical schedules.

9. The method of claim 1, wherein the surgical schedules are received at the remote server and the remote server predicts the required inventory level, the first CART located at a first facility and the second CART located at a second facility.

10. The method of claim 1, wherein the required inventory level is compared against the first and second CART inventory levels, the remote server configured to communicate with a manufacturer of at least one of the plurality of surgical items to provide replenishment information to the manufacturer based on the comparison of the required inventory level to the first and second CART inventory levels.

11. The method of claim 1, wherein the remote server analyzes the first and second CART inventory levels and the required inventory level to produce replenishment strategies, system-specific inventory and location groupings related to the plurality of surgical items.

12. The method of claim 1, wherein the first sensor is comprised of a first antenna array and a first plurality of tags of the plurality of tags are comprised are associated with the first plurality of surgical items, the first CART inventory level from the first CART based on the scan made by the first antenna array of the first plurality of tags.

13. The method of claim 12, wherein the first plurality of tags is comprised of a plurality of RFID tags, each of the first plurality of RFID tags associated with one of the first plurality of surgical items, the first CART inventory level from the first CART based on the scan made by the first antenna array of the first plurality of RFID tags.

* * * * *